United States Patent [19]

Trybulski et al.

[11] Patent Number: 5,880,122
[45] Date of Patent: Mar. 9, 1999

[54] 3-CARBOXAMIDE DERIVATIVES OF 5H-PYRROLO[2,1-C][1,4]-BENZODIAZEPINES

[75] Inventors: Eugene J. Trybulski, Princeton Junction; Albert J. Molinari; Jehan F. Bagli, both of Princeton; Mark A. Ashwell, Plainsboro, all of N.J.; Thomas J. Caggiano, Morrisville, Pa.

[73] Assignee: American Home Products Corporation, Madison, N.J.

[21] Appl. No.: 955,511

[22] Filed: Oct. 22, 1997

Related U.S. Application Data

[60] Provisional application No. 60/029,927 Nov. 1, 1996.
[51] Int. Cl.$^6$ .................... A61K 31/55; C07D 487/12
[52] U.S. Cl. ............................. 514/220; 540/561
[58] Field of Search .................. 540/561; 514/220

[56] References Cited

U.S. PATENT DOCUMENTS

| | | | |
|---|---|---|---|
| 4,766,108 | 8/1988 | Ali | 514/16 |
| 5,055,448 | 10/1991 | Manning et al. | 514/16 |
| 5,070,187 | 12/1991 | Gavras et al. | 530/315 |
| 5,258,510 | 11/1993 | Ogawa et al. | 540/276 |
| 5,436,333 | 7/1995 | Venkatesan et al. | 540/586 |
| 5,459,131 | 10/1995 | Albright et al. | 514/19 |
| 5,512,563 | 4/1996 | Albright et al. | 514/217 |
| 5,516,774 | 5/1996 | Albright et al. | 514/217 |
| 5,521,173 | 5/1996 | Venkatesan et al. | 514/220 |
| 5,532,235 | 7/1996 | Albright et al. | 514/215 |
| 5,536,718 | 7/1996 | Albright et al. | 514/220 |

FOREIGN PATENT DOCUMENTS

| | | |
|---|---|---|
| 0382185 | 2/1990 | European Pat. Off. |
| 0514667 | 4/1992 | European Pat. Off. |
| 0533240 | 9/1992 | European Pat. Off. |
| 0533242 | 9/1992 | European Pat. Off. |
| 0533243 | 9/1992 | European Pat. Off. |
| 0533244 | 9/1992 | European Pat. Off. |
| 0620216 | 4/1994 | European Pat. Off. |
| 9105549 | 5/1991 | WIPO . |
| 9412476 | 6/1994 | WIPO . |
| 9414796 | 7/1994 | WIPO . |
| 9404525 | 9/1994 | WIPO . |
| 9420473 | 9/1994 | WIPO . |

OTHER PUBLICATIONS

Burggraaf et al., *Cli. Sci.*, 86, 497–503 (1994).
Cash et al., *Brit. J. Haematol.*, 27, 363–364 (1974).
Cervoni and Chan, *Diuretic Agents*, in Kirk–Othmer, Encyclopedia of Chemical.
Technology, 4th ed., vol. 8, 398–432, (1993).
David, *Regulatory Peptides*, 45, 311–317 (1993).
du Vigneaud, Gish and Katsoyannis, *J. Am. Chem. Soc.*, 76, 4751–4752, (1954).
Goodman and Gilman, *The Pharmacological Basis of Therapeutics*, 9th ed., pp. 715–731 (1996).
Inanaga et al., *Bull. Chem. Soc. Jpn.*, 52, 1989 (1979).
*J. Med. Chem.*, 35, 382–388 (1992).
Lethagen, *Ann. Hematol.*, 69, 173–180 (1994).
Lin et al., *J. Chin. Chem. Soc.*, 40, 273–282 (1993).
Manning M. et al., *J. Med. Chem.*, 35, 3895–3904 (1992).
Oliver and Schaefer, *J. Physiol. (London)*, 18, 277–279 (1895).
Ruffolo, R.R. et al., *Drug News and Perspective*, 4(4), 217–222, (May 1991).
Timari et al., *Chem. Ber.*, 125, 929–932 (1992).
Williams, P.D. et al., *J. Med. Chem.*, 35, 3905–3918 (1992).
Yamamura, Y. et al., *Br. J. Pharmacol*, 105, 787–791 (1992).

*Primary Examiner*—Mukund J. Shah
*Assistant Examiner*—Bruck Kifle
*Attorney, Agent, or Firm*—Steven R. Eck

[57] ABSTRACT

This invention relates to tricyclic non-peptide vasopressin antagonists which are useful in treating conditions where decreased vasopressin levels are desired, such as in congestive heart failure, in disease conditions with excess renal water reabsorption and in conditions with increased vascular resistance and coronary vasoconstriction, the compounds having the general structure:

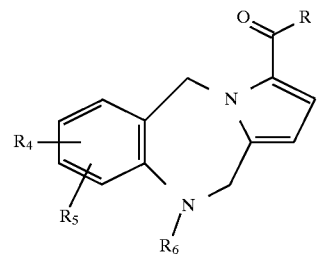

32 Claims, No Drawings

3-CARBOXAMIDE DERIVATIVES OF 5H-PYRROLO[2,1-C][1,4]-BENZODIAZEPINES

This application claims the benefit of U.S. Provisional Application No. 60/029,927, filed Nov. 1, 1996.

This invention relates to new tricyclic non-peptide vasopressin antagonists which are useful in treating conditions where decreased vasopressin effects are desired, such as in congestive heart failure, in disease conditions with excess renal water reabsorption and in conditions with increased vascular resistance and coronary vasoconstriction.

BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its action through two well defined receptor subtypes: vascular $V_{1a}$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_{1a}$ receptor antagonists may decrease systemic vascular resistance, increase cardiac output and prevent vasopressin induced coronary vasoconstriction. Thus, in conditions with vasopressin induced increases in total peripheral resistance and altered local blood flow, $V_{1a}$ receptor antagonists may be therapeutically useful agents. $V_{1a}$ receptor antagonists may decrease blood pressure, induce hypotensive effects and thus be therapeutically useful in treatment of some types of hypertension.

The blockade of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylate cyclase and promotes the cAMP-mediated incorporation of water pores into the luminal surface of these cells. $V_2$ antagonists may correct the fluid retention in congestive heart failure, liver cirrhosis, nephritic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone, On the basis of biochemical and pharmacological effects of the hormone, antagonists of vasopressin are expected to be therapeutically useful in the treatment and/or prevention of hypertension, cardiac insufficiency, coronary vasospasm, cardiac ischemia, renal vasospasm, liver cirrhosis, the syndrome of inappropriate anti-diuretic hormone secretion (SIADH), congestive heart failure, nephritic syndrome, brain edema, cerebral ischemia, cerebral hemorrhage-stroke, thrombosis-bleeding and abnormal states of water retention.

The following prior art references describe peptide vasopressin antagonists: M. Manning et al., *J. Med. Chem.*, 35, 382(1992); M. Manning et al., *J. Med. Chem.*, 35, 3895 (1992); H. Gavras and B. Lammek, U.S. Pat. No. 5,070,187 (1991); M. Manning and W. H. Sawyer, U.S. Pat. No. 5,055,448(1991) F. E. Ali, U.S. Pat. No. 4,766,108(1988); R. Ruffolo et al., *Drug News and Perspective*, 4(4), 217, (May)(1991). P. D. Williams et al., have reported on potent hexapeptide oxytocin antagonists [*J. Med. Chem.*, 35, 3905 (1992)] which also exhibit weak vasopressin antagonist activity on binding to $V_1$ and $V_2$ receptors. Peptide vasopressin antagonists suffer from a lack of oral activity and selectivity. Some exhibit partial agonist activity.

Non-peptide vasopressin antagonists have recently been disclosed, Y. Yamamura et al., *Science*, 252, 579(1991); Y. Yamamura et al., *Br. J. Pharmacol*, 105, 787(1992); J. D. Albright et al. U.S. Pat. No. 5,536,718A, U.S. Pat. No. 5,532,235A, U.S. Pat. No. 5,516,774A, U.S. Pat. No. 5,512,563A, U.S. Pat. No. 5,459,131A; A. Venkatessan et al. U.S. Pat. No. 5,521,173A; Ogawa et al., (Otsuka Pharm Co., LTD.) EP 0514667-A1, EPO 382185-A2, WO 9105549 and U.S.5,258,510, WO 9404525; Yamanouchi Pharm.Co.,Ltd., WO 9420473, WO 9412476, WO 9414796; Fujisawa Co. Ltd., EP 620216-A1; Ogawa et al, (Otsuka Pharm. Co.). EP 470514A disclose carbostyril derivatives and pharmaceutical compositions containing the same. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP 0533240A; K. Gilbert et al., EP 0533243A. U.S. Pat. No. 5,436,333 (Venkatesan et al.) teaches a process for the preparation of tricyclic heterocycles which are useful as intermediates in the production of cardiovascular agents.

The present invention relates to novel tricyclic derivatives which exhibit vasopressin antagonist activity, in vitro at the $V_2$ receptors and exhibit in vivo vasopressin antagonist activity. In addition these compounds possess enhanced water solubility when compared to previously described 3-acylpyrrolobenzodiazepine derivatives.

BRIEF DESCRIPTION OF THE INVENTION

This invention relates to novel compounds selected from those of the general formula I:

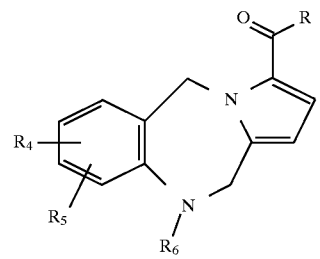

where

R is selected from —OH, —NR$_1$R$_3$, —NHOR$_1$—N—(CH$_2$)$_n$—COOH,

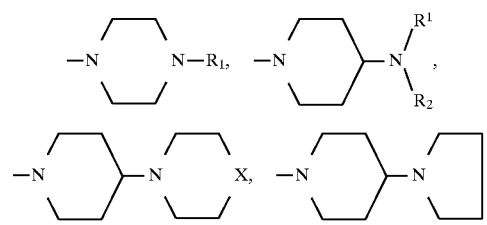

-continued

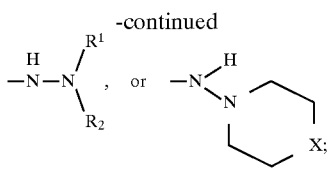

$R_1$ and $R_2$ are, independently, hydrogen or lower alkyl;
$R_3$ is

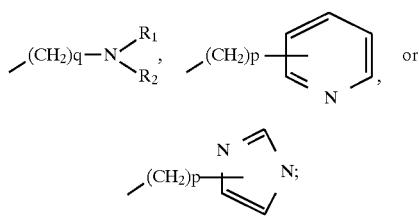

X is $CH_2$, $NR_2$, O, S;
n is 1 to 4;
p is 1 to 4;
q is 2to 4;

$R_4$ and $R_5$ are, independently, selected from hydrogen, lower alkyl, halogen, cyano, trifluoromethyl, amino, hydroxy, or lower alkoxy;

$R_6$ is a moiety of the formula:

Ar is a moiety selected from

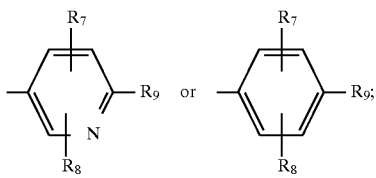

$R_7$ and $R_8$ are independently selected from hydrogen, halogen, cyano, lower alkyl, lower alkoxy, hydroxy, or trifluoromethyl;

$R_9$ is a moiety of the formula:

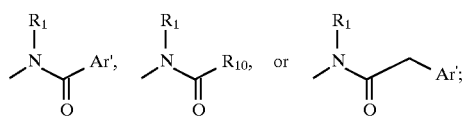

$R_{10}$ is selected from $C_3$–$C_7$ cycloalkyl, cyclopentenyl, cyclohexenyl, or the moiety of the formula

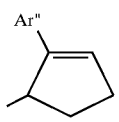

Ar' is a moiety selected from

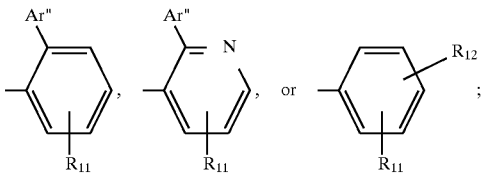

Ar" is selected from
1. phenyl;
2. a five membered aromatic (unsaturated) heterocyclic ring having one or two heteroatoms selected from N, O, S;
3. a five membered aromatic (unsaturated) heterocyclic ring having three or four nitrogen atoms; or
4. a six membered aromatic (unsaturated) heterocyclic ring having one, two or three nitrogen atoms;
and the Ar" may be optionally substituted with halogen, lower alkyl, hydroxy, lower alkoxy, or trifluoromethyl; or the pharmaceutically acceptable salts, esters or prodrug forms thereof.

For the purposes of this specification, lower alkyl is $C_1$ to $C_6$, preferably $C_1$ to $C_4$, straight or branched chain alkyl, such as methyl, ethyl, n-butyl, tert-butyl, and lower alkoxy is $C_1$ to $C_6$, preferably $C_1$ to $C_4$, straight or branched chain alkyloxy, such as methoxy, ethoxy, n-butoxy, or tert-butoxy. Halogen is fluorine, chlorine, bromine, or iodine. Cycloalkyl refers to $C_3$ to $C_7$ monocyclic cycloalkyl moieties.

It will be understood that the Ar" substituents of this invention which are five membered aromatic (unsaturated) heterocyclic ring having one or two heteroatoms selected from N, O, S include, but are not limited to, thienyl, furyl, pyrrolyl, pyrazolyl, oxazolyl, thiazolyl, isothiazolyl, isoxazolyl, and imidazolyl groups. The Ar" groups comprising a five membered aromatic (unsaturated) heterocyclic ring having three or four nitrogen atoms include the triazole and tetrazole moieties. The Ar" groups comprising a six membered aromatic (unsaturated) heterocyclic ring having one, two or three nitrogen atoms include, but are not limited to, pyridyl, pyrazinyl, pyrimidinyl, pyridazinyl, 1,2,3-triazine, 1,2,4-triazine, and 1,3,5-triazine groups.

Among the more preferred compounds of this invention are those having the following Formula I:

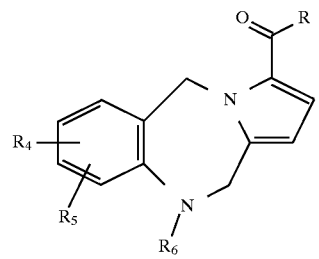

wherein
R is selected from —OH, —$NR_1$ $R_3$, —N—$(CH_2)_n$—COOH,

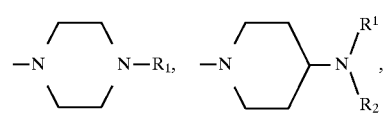

-continued

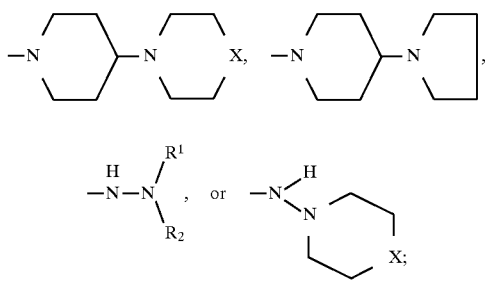

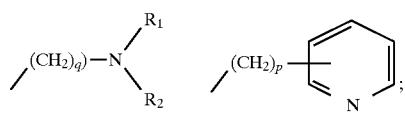

$R_1$ and $R_2$ are, independently, hydrogen or lower alkyl;

$R_3$ is

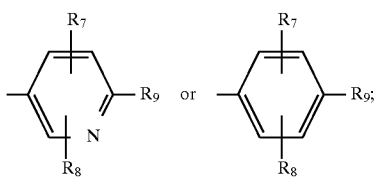

X is $CH_2$, $NR_1$, O, S;

n is 1 to 4;

q is 2 to 4;

$R_4$ and $R_5$ are independently selected from the group of hydrogen, lower alkyl, halogen, amnino, hydroxy, cyano, trifluormethyl, or lower alkoxy;

$R_6$ is a moiety of the formula:

Ar is a moiety selected from

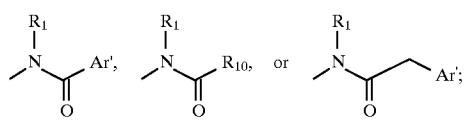

$R_7$ and $R_8$ are independently selected from hydrogen or halogen;

$R_9$ is a moiety of the formula:

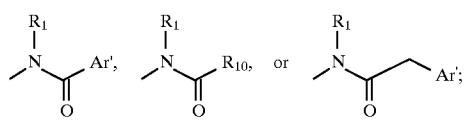

$R_{10}$ is a moiety of the Ar" formula:

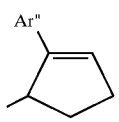

Ar' is a moiety selected from

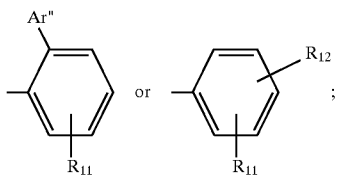

$R_{11}$, $R_{12}$ are selected independently from hydrogen, F, Br, Cl, or lower alkyl;

Ar" is selected from phenyl or a five membered aromatic (unsaturated) heterocyclic ring having one or two heteroatoms selected from N, O, S;

or a pharmaceutically acceptable salt, ester or prodrug form thereof.

Even more preferred compounds of this invention are those of the formula:

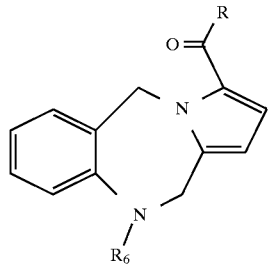

wherein R is selected from OH, $NR_1R_3$ or

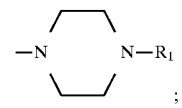

$R_9$ is

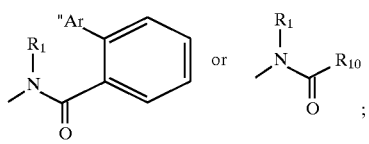

$R_{10}$ is 2-Ar"-cyclopentenyl;

and $R_1$, $R_2$, $R_3$, $R_6$, $R_7$, $R_9$, $R_{10}$, $R_{11}$, $R_{12}$, X, n, p, q, Ar, Ar', and Ar" are as defined in the most generic group, above, and more preferably, as defined in the subgeneric group, above; or the pharmaceutically acceptable salts, esters or prodrug forms thereof.

DETAILED DESCRIPTION OF THE INVENTION

The present invention comprises the compounds described above, as well as pharmaceutical compositions containing the compounds and one or more pharmaceutically acceptable carriers, excipients, etc. This invention also comprises methods for treating conditions in a mammal, preferably in a human, where decreased vasopressin effects are desired, the methods comprising administering to a mammal in need thereof a therapeutically effective amount of one or more of the compounds of this invention.

The compounds of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, citric acid, tartaric acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo. When the compounds are employed for the above utilities, they may be combined with one or more pharmaceutically acceptable excipients or carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of mammal body weight, preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard- filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

As mentioned above, the new tricyclic non-peptide vasopressin antagonists of this invention are useful in treating conditions where decreased vasopressin effects are desired, such as in congestive heart failure, in disease conditions with excess renal water reabsorption and in conditions with increased vascular resistance and coronary vasoconstriction.

In particular, the vasopressin antagonists of this invention are therapeutically useful in the treatment and/or prevention of hypertension, cardiac insufficiency, coronary vasospasm, cardiac ischemia, renal vasospasm, liver cirrhosis, the syndrome of inappropriate anti-diuretic hormone secretion (SIADH), congestive heart failure, nephritic syndrome, brain edema, cerebral ischemia, cerebral hemorrhage-stroke, thrombosis-bleeding and abnormal states of water retention.

Compounds, of this invention, 3-acylated pyrrolobenzodiazepine derivatives 7 (Scheme I), may be prepared using two procedures from a common 3-trihalomethylketone derivative (e.g. 4). The synthesis of this intermediate and it's precursor have been described (EP 636625 A2). Reaction of the 3-trihalomethylketone derivative 4 directly with a primary or secondary amine provides the desired product 7. Alternately, the 3-trihalomethylketone derivative 4 is treated with aqueous base, such as sodium hydroxide, to obtain, on acidification, the corresponding carboxylic acid 5. The carboxylic acid group may be activated for coupling by conversion to an acid chloride, bromide or anhydride or by first reacting with an activating reagent such as N,N-dicyclohexylcarbodiimide, diethyl cyanophosphonate and related activating reagents used in "peptide amide bond" formation. The method of activating the acids is chosen on the basis of compatibility with other substituent groups in the molecule. One example may be the treatment of acid 5 with oxalyl chloride/dimethylformamide to afford the acid chloride 6 which when treated with a primary or secondary amine, provides the desired product 7, wherein $-NZ_1Z_2$, may be $-NR_1R_3$, $NHOR_1$, $-N-(CH_2)_n-COOH$,

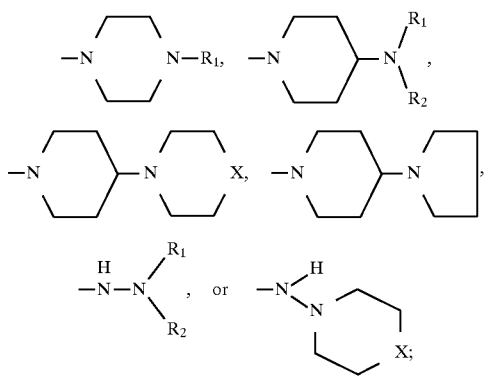

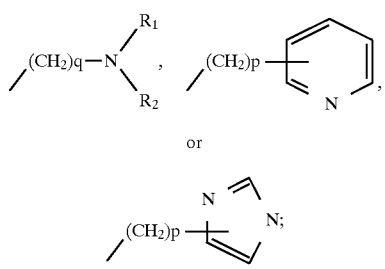

$R_1$ and $R_2$ are, independently, hydrogen or lower alkyl;
$R_3$ is

X is $CH_2$, $NR_1$, O, S;
n is 1 to 4;
p is 1 to 4;
q is 2 to 4;

The 3-trihalomethylketone derivative 4 is obtained by the acylation of the 3-position of the pyrrolobenzodiazepine 3 using the appropriate trihaloacetyl halide reagent. The 3-unsubstituted compound 3 may be either a fully assembled target compound where $R_{17}$ is selected from $R_6$ of Formula I or an intermediate where $R_{17}$

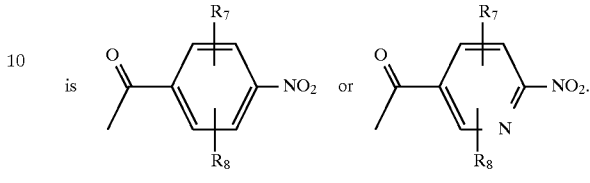

In the case where $R_{17}$ is

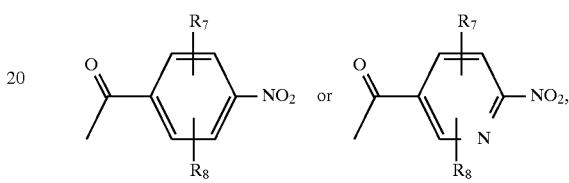

the compound can be prepared by following the procedures described in Scheme II, followed by the appropriate steps in Scheme I.

Compounds of general formula 4a and 4b may be prepared as shown in Scheme II. Reaction of tricyclic derivative 1 with a substituted or unsubstituted 4-nitroaryl carbonyl chloride or 6-nitropyridine-3-carbonyl chloride gave intermediate 8a or 8b. Reduction of the nitro group in the intermediates 8a and 8b afforded the corresponding amino derivatives 9a and 9b. The reduction of the nitro group in 8a Scheme I

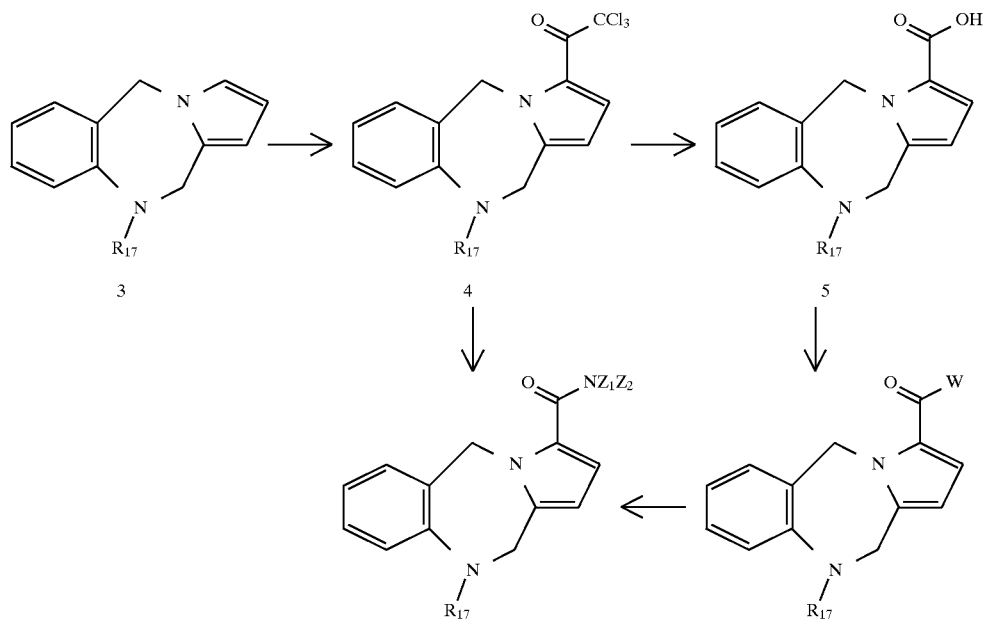

and 8b may be carried out under conditions of catalytic reduction (i.e. hydrogen/Pd/C, hydrazine-ethanol /Pd/C) or under chemical reduction conditions (i.e. stannous chloride/ethanol, zinc/acetic acid-titanium trichloride) or related reduction conditions known in the art. The conditions for the conversion of nitro to amino group are chosen on the basis of compatibility with the preservation of the other functional groups in the molecules.

The pyridine and aryl carboxylic acid reagents

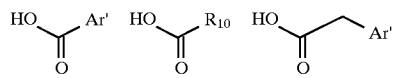

are activated for coupling by conversion to an acid chloride, bromide or anhydride or by first reacting with an activating reagent such as N,N-dicyclocarbodiimide, diethyl cyanophosphonate and related activating reagents used in "peptide amide bond" formation. The method of activating the acids for coupling to the tricyclic derivatives 9a and 9b is chosen on the basis of compatibility with other substituent groups in the molecule. The method of choice is the conversion of the carboxylic acids to the corresponding acid chlorides. The acid chlorides

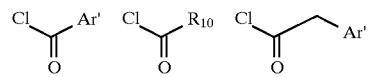

may be prepared by standard procedures known in the art, such as reaction with thionyl chloride, oxalyl chloride and the like. The coupling reaction is carried out in halogenated solvents such as chloroform, dichloromethane, ethereal solvents such as dioxane, tetrahydrofuran or hydrocarbon solvents such as toluene in the presence of pyridine or tertiary amine bases such as triethylamine and the like Alternatively, acid chlorides, prepared from the carboxylic acids, may be reacted with derivatives 9a and 9b in pyridine with or without 4-(dimethylamino)pyridine to afford compounds 10a and 10b.

Reaction of compounds of formula 9a and 9b with aroyl, arylacetyl, or cycloalkenyl carbonyl chloride or the corresponding activated carboxylic acids; in halogenated solvents such as chloroform, dichloromethane, ethereal solvents such as dioxane, tetrahydrofuran or hydrocarbon solvents such as toluene; in the presence of a tertiary amine base such as triethylamine, diisopropylethylamine or pyridine and the like affords the derivatives 10a and 10b. The reaction of derivatives 10a and 10b with trihalomethylacyl chloride in an inert solvent such as chloroform, dichloromethane or an ethereal solvent such as tetrahydrofuran between 0° and the reflux temperature of the solvents affords the trihalomethyl ketone derivatives 4a and 4b.

Scheme II

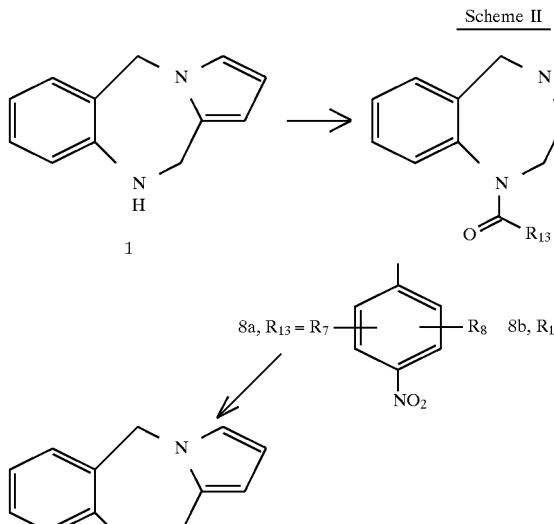

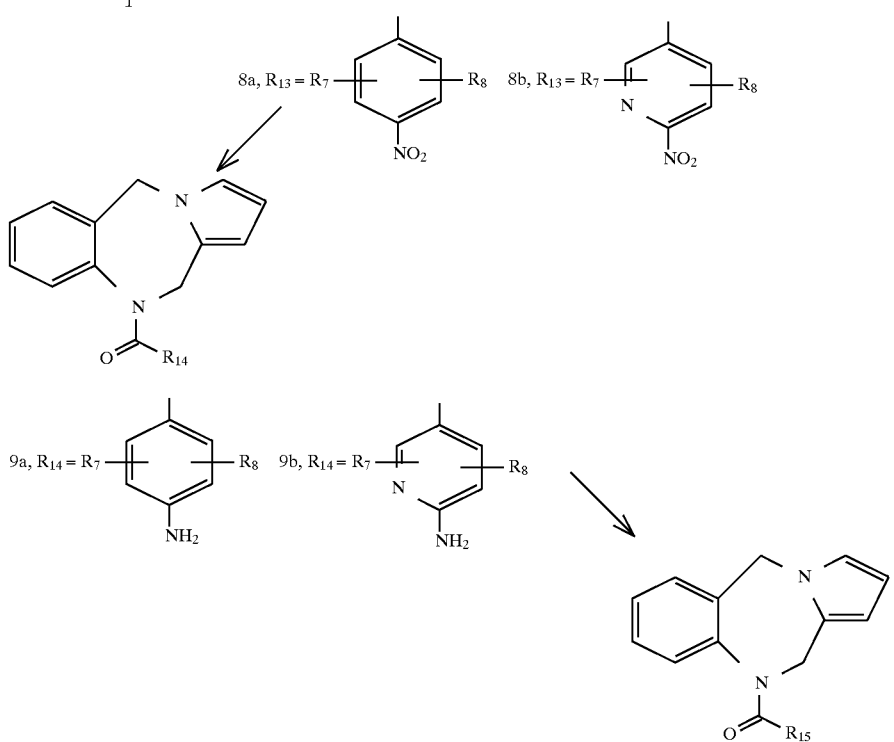

-continued
Scheme II

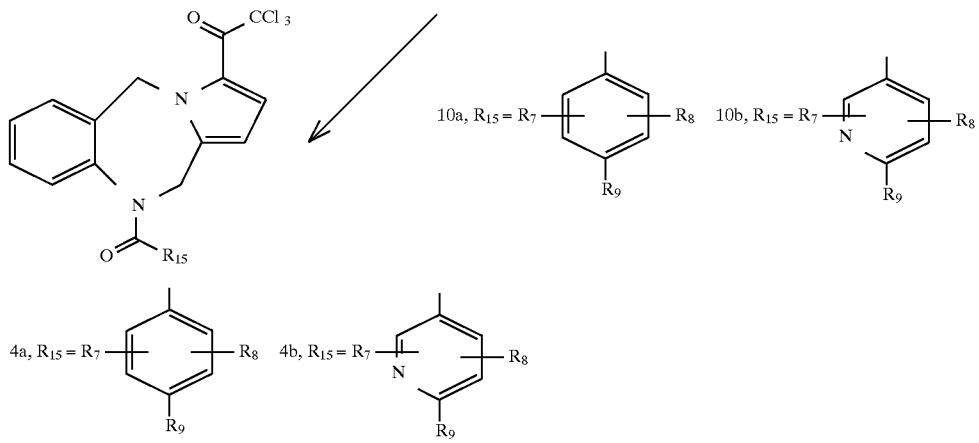

An alternate sequence of steps can be utilized to prepare the title compounds as shown in Scheme IIb. Reduction of the nitro group in the intermediates 12a and 12b, wherein—$NZ_1Z_2$, may be —$NR_{13}$, $NHOR_1$, —$N$—$(CH_2)_n$—COOH, and $R_7$ and $R_8$ are independently selected from hydrogen, halogen, cyano, lower alkyl, lower alkoxy, hydroxy, or trifluoromethyl afforded the corresponding amino derivatives 13a and 13b. The reduction of the nitro group in 12a and 12b may be carried out under conditions of catalytic reduction (i.e. hydrogen/Pd/$C_1$ hydrazine-ethanol /Pd/C) or under chemical reduction conditions (i.e. stannous chloride/ethanol, zinc/acetic acid-titanium trichloride) or related reduction conditions known in the art. The conditions for the conversion of nitro to amino group are chosen on the basis of compatibility with the preservation of the other functional groups in the molecules. Acylation of amino derivatives 13a and 13b with the appropriately substituted and activated pyridine and aryl carboxylic acids afforded the target compounds 14a and 14b The pyridine and aryl carboxylic acid reagents

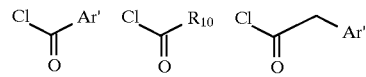

are activated for coupling by conversion to an acid chloride, bromide or anhydride or by first reacting with an activating reagent such as N,N-dicyclocarbodiimide, diethyl cyanophosphonate and related activating reagents used in "peptide amide bond" formation. The method of activating the acids for coupling to the tricyclic derivatives 13a and 13b is chosen on the basis of compatibility with other substituent groups in the molecule. The method of choice is the conversion of the carboxylic acids the corresponding acid chlorides. The acid chlorides may be prepared by standard procedures known in the art, such as reaction with thionyl chloride, oxalyl chloride and the like. The coupling reaction is carried out in solvents such as halogenated hydrocarbons, toluene, xylene, tetrahydrofuran, or dioxane in the presence of pyridine or tertiary amine bases such as triethylamine and the like Alternatively, acid chlorides prepared from the carboxylic acids, may be reacted with derivatives 13a and 13b in pyridine with or without 4-(dimethylamino)pyridine to afford compounds 14a and 14b.

Scheme IIb

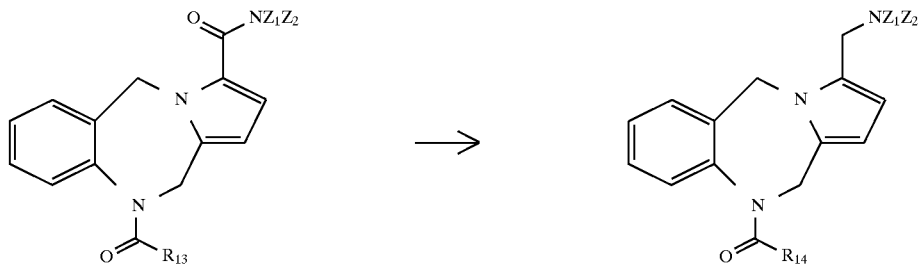

-continued
Scheme IIb

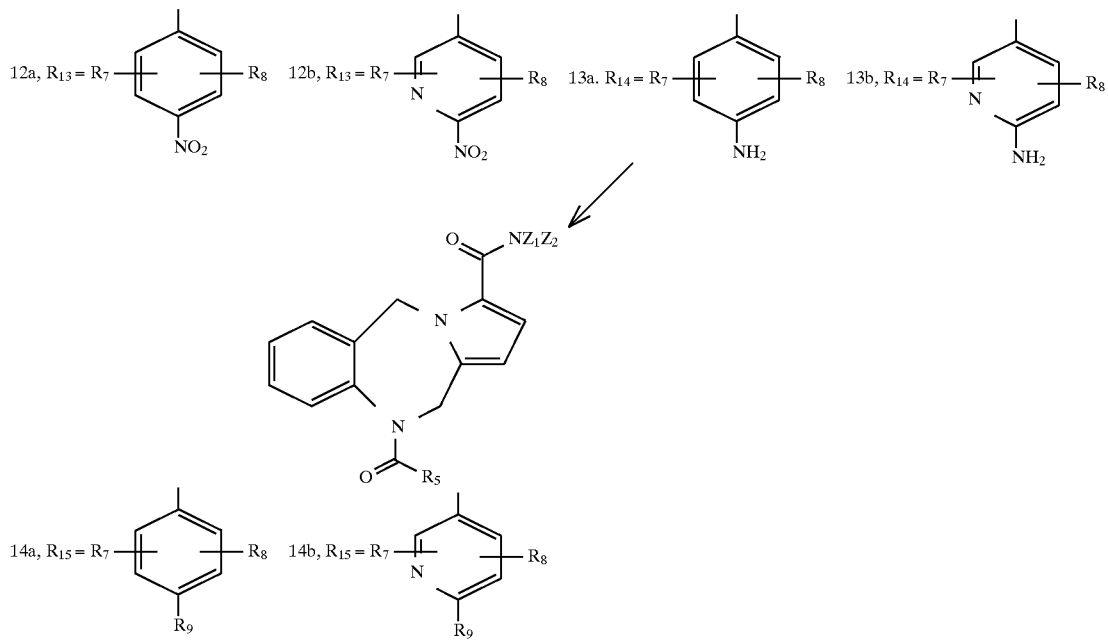

Alternatively the intermediates 1 (Scheme III) may be converted to the more reactive fluoride derivatives 15. The reaction of 15 with a substituted amine $NHR_1(R_1=$lower alkyl) gives the corresponding aminonicotinyl derivatives 16. Acylation of these derivatives 16 leads to the target molecule 17. This compound can be treated with trihalomethyl acetyl chloride to give corresponding products of formula 4b of Scheme II.

Scheme III

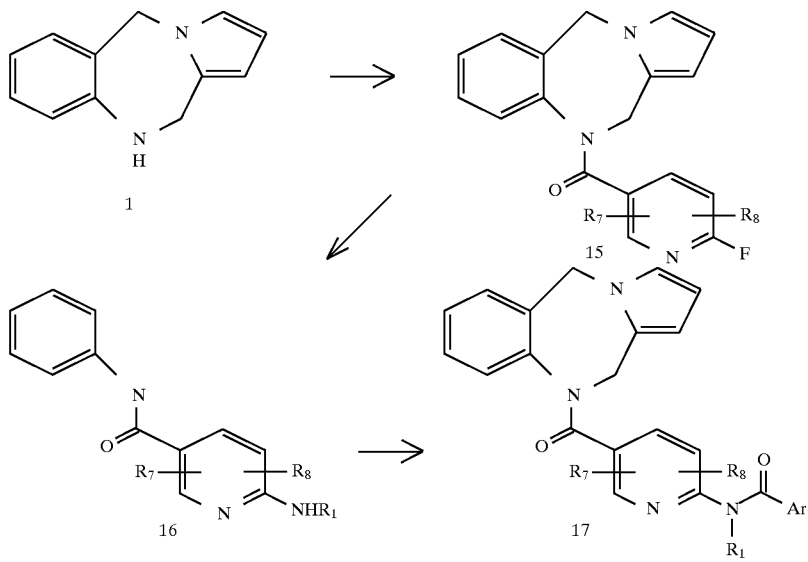

As an alterative method for the synthesis of compounds of this invention a s depicted in Formula I where $R_6$ is as shown below

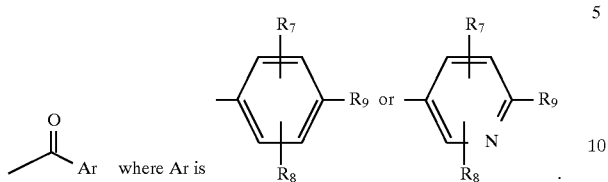

Coupling of pyridyl or aryl carboxylic acids of general formula 18 with the tricyclic derivatives 1 will give target compounds 20, which when reacted with trihalomethyl acetyl chloride gives the intermediate 4 of Scheme I.

The pyridine and aryl carboxylic acids are activated for coupling by conversion to an acid chloride, bromide or anhydride or by first reacting with an activating reagent such as N,N-dicyclocarbodiimide, diethyl cyanophosphonate and related activating reagents used in "peptide amnide bond" formation . The method of activating the acids 18 for coupling to the tricyclic derivatives 1 (Scheme IV) is chosen on the basis of compatibility with other substituent groups in the molecule. The method of choice is the conversion of the carboxylic acids 18 to the corresponding acid chlorides 19. The acid chlorides 19 may be prepared by standard procedures known in the art, such as reaction with thionyl chloride, oxalyl chloride and the like. The coupling reaction is carried out in halogenated solvents such as chloroform, dichloromethane, ethereal solvents such as dioxane, tetrahydrofuran or hydrocarbon solvents such as toluene in the presence of pyridine or tertiary amine bases such as triethylamine and the like (Scheme IV). Alternatively, acid chlorides 19, prepared from the carboxylic acids, may be reacted with derivatives 1 in pyridine with or without 4-(dimethylamino)pyridine.

In general, when the acids 18 are activated with "peptide type" activating reagents, higher temperatures are required than when the acid chlorides are used.

Scheme IV

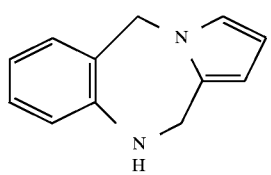

1

-continued
Scheme IV

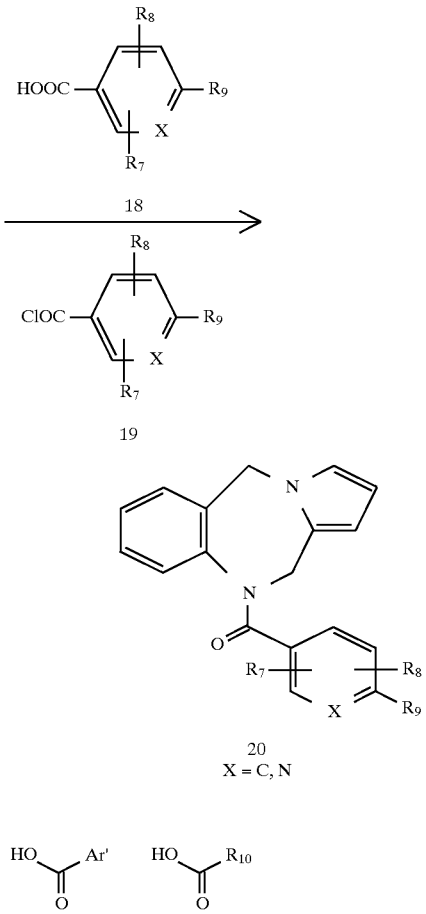

The acids (represented in part by 23, 26, 29) may be prepared by the methods shown in Scheme V.

Scheme V

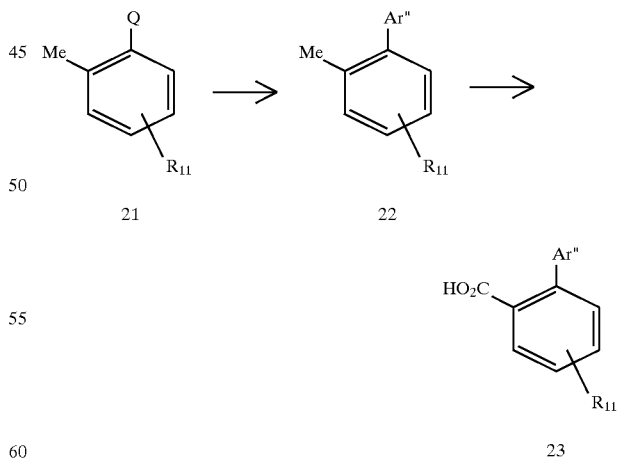

-continued
Scheme V

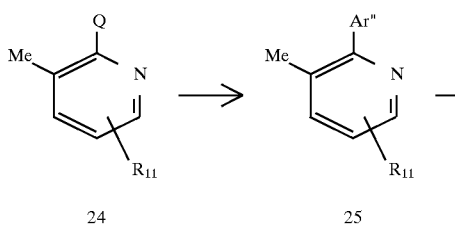

24    25

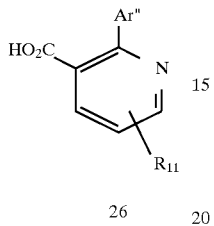

26

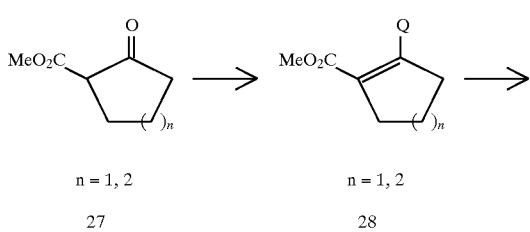

27    28

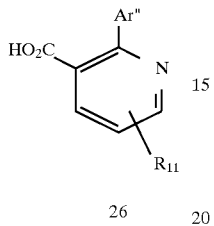

29

An aryl (or heteroaryl) borane, borate, magnesium, trialkyltin, or zinc reagent is coupled to an aryl 21, or pyridyl 24 compound, where Q is selected from bromine, iodine, fluorosulfonate or trifluoromethylsulfonate and $R_{11}$ is hydrogen, fluorine, chlorine or bromine, using a zerovalent palladium or nickel catalyst in the presence or absence of coordinating ligands such as triphenylphosphine and an organic or inorganic base. The resulting methyl bis aryl (heteroarylaryl) 22 or arylpyridyl (heteroarylpyridyl) 25 compound can then be oxidized using reagents such as $KMnO_4$ to provide the corresponding carboxylic acids 23 and 26. Derivatives of 23 and 26 where $R_{11}$ is lower alkyl can be prepared by treatment of the methyl ester of 23 and 26, where $R_{11}$ is bromine with the corresponding lower alkylborane in the presence of a zerovalent palladium catalyst.

In the case of cycloalkyl moiety, compound 29, the material can be prepared starting from the appropriate ketoester 27. Reaction of keto ester 27 with phosphorous trihalide (bromo, iodo) or triflic anhydride, for example, affords the corresponding β-halo or β-trifluoromethylsulfonate compound 28. Compound 28 can be reacted with an aryl (heteroaryl) borane, borate, magnesium, trialkyltin or zinc reagent in the presence of a zerovalent palladium or nickel catalyst and an organic or inorganic base to give the target compound 29 as the ester. Hydrolysis of the ester moiety in 29 with an alkali metal hydroxide in an aqueous alcohol or ether solvent provides the carboxylic acid 29.

Alternatively, compound of general formula I can be elaborated as shown in Scheme VI where J is selected from $B(OH)_2$, $Sn(lower\ alkl)_3$, $R_{16}$ is selected from Br, I, $OSO_2CF_3$, and Ar" is selected as defined above.

Scheme VI

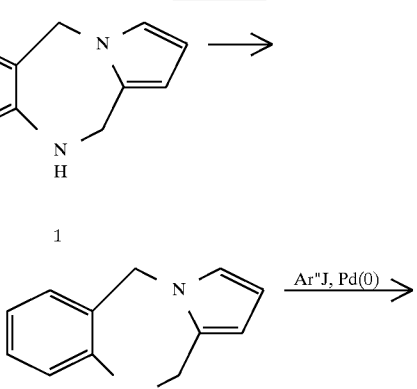

1

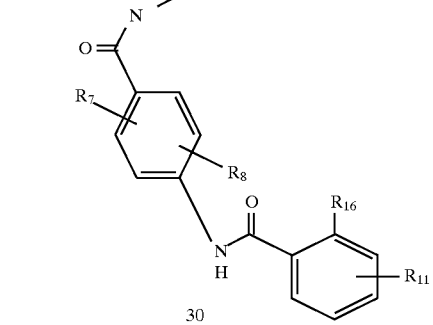

30

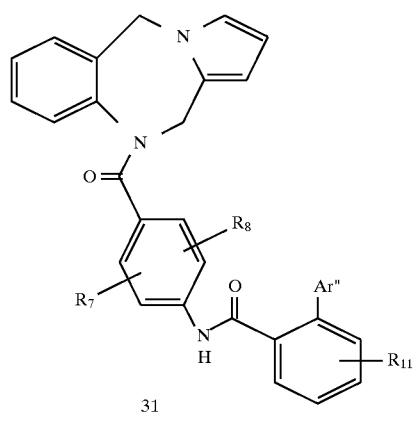

31

Intermediate 30 can be coupled to an aryl tin or boron reagent under the conditions of Stille or Suzuki, respectively, using zerovalent palladium in the presence or absence of coordinating ligands and a base to give compounds of general formula 31.

The present invention will be further understood in view of the following non-limiting examples.

EXAMPLE 1

10-[2-Chloro-4-(5-fluoro-2-methyl-benzoylamino)-benzoyl]-10,11-dihydro-5H-pyrrolor[2,1-c][1,4]benzodiazepine-3-carboxylic acid Step a) N-{3-Chloro-4-[3-(trichlorocarbonyl)-(5H,11H-pyrrolo[2,1-c][1,4]benzodiazepin-10-carbonyl]-phenyl}-5-fluoro-2-methyl-benzamide A suspension of N-[3-chloro-4-(5H, 11H-pyrrolo[2,1-c][1,4]benzodiazepin-10-carbonyl)-phenyl]-5-fluoro-2-methylbenzamide (4.73 g, 10 mmol) in dichloromethane (300 ml) was stirred at room temperature with trichloroacetyl chloride (1.81 g, 10 mmol) for 6 hours under nitrogen. A second equivalent of trichloroacetyl choride (1.81 g, 10 nmuol) was added, and the reaction stirred at room temperature overnight. After dilution with dichloromethane (500 ml), the reaction mixture was filtered through a silica gel plug (2×), and the filtrate evaporated in vacuo to a residue. The residue was redissolved in dichloromethane (300 ml), washed with 0.5N sodium hydroxide and water, and dried (MgSO4). Filtration through a silica gel plug (2×), and evaporation of the filtrate in vacuo afforded 6.2 g (10 mmol) of the 3-trichlormethyl ketone as a tan amorphous powder, which was used without further purification in Example 1, step b.
Step b) 10-[2-Chloro-4-(5-fluoro-2-methyl-benzoylamino)-benzoyl]-10,11-dihydro-5H-pyrrolo[2,1-c][1,4]benzodiazepine-3-carboxylic acid N-{3-Chloro-4-[3-(trichlorocarbonyl)-(5H,11H-pyrrolo[2,1-c][1,4]-benzo-diazepin-10-carbonyl]-phenyl}-5-fluoro-2-methyl-benzamide (1.22 g, 2 mmol) was stirred in acetone (5 ml) under nitrogen at room temperature for 45 minutes with 2.5N sodium hydroxide (1.6 ml, 4 mmol). The reaction mixture was neutralized to pH 7.0 with 2N HCl (2 ml, 4 mmol). After addition of water (10 ml), the precipitate was filtered, washed sequentially with cold water, ethanol, and diethyl ether to afford, after air-drying, a crude product as a colorless powder (750 mg, 72%). Recrystallization of the crude product from methanol-water (3:1, 10 ml) afforded, after drying in vacuo at 25° C. for three hours, 600 mg (1.2 mmol) of the title compound as homogeneous colorless crystalline solid, m.p. 218° C. (dec). MS (+FAB), m/z: 520/518 (M+H).

Analysis for: $C_{28}H_{21}ClFN_3O_4 \cdot 0.62\ H_2O$ Calcd: C, 63.55; H, 4.24; N, 7.94. Found: C, 63.53; H, 4.21; N, 7.82.

EXAMPLE 2

10-[2-Chloro-4-(5-fluoro-2-methyl-benzoylamino)-benzoyl]-10,11-dihydro-5H-pyrrolo[2,1-c][1,4]benzodiazepine-3-carboxylic acid, potassium salt (1:1)

A suspension of the product of Example 1, step b, 10-[2-Chloro-4-(5-fluoro-2-methyl-benzoylarnino)-benzoyl]-10,11 -dihydro-5H-pyrrolo[2,1-c][1,4]benzodiazepine-3-carboxylic acid (517 mg, 1 mmol), in methanol (10 ml) was treated with 1N potassium hydroxide (1 ml, 1 mmol), and filtered. After evaporation of the solvent in vacuo, the residue was redisssolved in acetone (50 ml), refiltered (2×), and concentrated to a smaller volume (20 ml). Addition of diethyl ether and cooling afforded, after filtration of the solid and drying in vacuo at 70° C. for three hours, 270 mg (0.49 mmol) of the potassium salt of the acid as a slightly colored amorphous powder, m.p. 195–205° C.

MS (+FAB), m/z: 520/518 (M+H). Analysis for: $C_{28}H_{20}ClFKN3O_4$ 3.2 $H_2O$. Calcd: C, 60.48; H, 3.63; N, 7.56. Found: C, 59.22; H, 4.03; N, 7.30.

EXAMPLE 3

N-{3-Chloro-4-[3-(N', N'-dimethyl-pydrazinocarbonyl)-5H,11H-pyrrolo[2,1-c][1,4]benzodiazepine-10-carbonyl]-phenyl}-5-fluoro-2-methyl-benzamide N-{3-Chloro-4-[3-(trichlorocarbonyl)-(5H,11H-pyrrolo[2,1-c][1,4]benzo-diazepin-10-carbonyl]-phenyl}-5-fluoro-2-methyl-benzamide (1.86 g, 3 mmol) was stirred under nitrogen with excess N, N-dimethylhydrazine (5 ml) for 3 hours at 60° C. The excess N, N-dimethylhydrazine was removed under high vacuum. The residue was dissolved in ethyl acetate, filtered through a short silica gel plug, and the filtrate evaporated in vacuo, to afford 1.63 g (2.9 mmol, 97%) of a crude product. Purification by flash column chromatography on silica gel (150 g), and eluting with ethyl acetate, afforded, after drying in vacuo at 25° C. overnight, 1.15 g (2,1 mmol) of the title compound as a light yellow amorphous powder, retaining 0.33 mole of ethyl acetate, m.p. 133–135° C.

MS (–ESI), m/z: 560/558 (M–H)⁻. Analysis for: $C_{30}H_{27}ClFN_5O_3 \cdot 0.33\ C_4H_8O_2$. Calcd.: C,63.85; H, 5.07; N, 11.88. Found: C, 63.17; H, 5.10; N, 11.77.

EXAMPLE 4

2-[[10-[2-Chloro-4-[(5-fluoro-2-methybenzoyl)amino]benzoyl]-10,11-dihdro-5H-pyrrolo{2,1-cl[4,1]benzodiazepin-3-yl]carbonyl]-1,1,1-trimethylhydrazinium iodide The product of Example 3, N-{3-Chloro-4-[3-(N', N'-dimethyl-hydrazinocarbonyl)-5H,11H-pyrrolo[2,1, -c][1, 4]benzodiazepine- 10-carbonyl]-phenyl }5-fluoro-2-methyl-benzamide (700 mg, 1.25 mmol) was treated with excess iodomethane (5 g, 35 mmol) in dichloromethane (100 ml) and stirred under nitrogen at room temperature for 60 hours. The precipitate was filtered, and washed sequentially with cold dichloromethane and diethyl ether to afford, after drying in vacuo at 25 ° C. overnight, 700 mg (1.0 mmol) of the title compound as a colorless amorphous powder, m.p. (188) 193° C.

MS (–ESI), m/z: 828 (MI+I)⁻ MS (+FAB), m/z: 574 (M+H)⁺

Analysis for: $C_{31}H_{30}ClFIN_5O_3 \cdot H_2O \cdot 0.6CH_2Cl_2$. Calcd: C, 49.23; H, 4.34; N, 9.08; I, 16.47. Found: C, 48.83; H, 4.00; N, 9.11; I, 17.02.

EXAMPLE 5

2-[[10-[2-Chloro-4-[(5-fluoro-2-methylbenzoyl)amino]benzoyl]-10,11-dihydro-5H-pyrrolo[2,1-c][1,4]benzodiazepin-3-yl]hydroxymethylenel-1.1,1-trimetpylpydrazinium inner salt The product of Example 4, 2-[[10-[2-Chloro-4-[(5-fluoro-2-methylbenzoyl)-amino]bnezol]-10,11 -dihydro-5H-pyrrolo (2,1-c][1,4]benzodiazepin-3-yl]carbonyl 1,1,1-trimethylhydrazinium iodide (400 mg, 0,57 mmol), was treated with 0.1N sodium hydroxide (5.7 ml, 0.57 mmol) in a mixture of methanol-water (10 ml: 10 drops). After concentration in vacuo, additional water was added. The precipitate was filtered, and washed sequentially with water, cold methanol, and diethyl ether to afford, after drying in vacuo at 25° C. for 5 hours, 160 mg (0.28 mmol) of the title compound as a colorless amorphous powder, m.p. 255° C. MS (+ESI), m/z: 576/574 (M+H)⁺.

Analysis for: $C_{31}H_{29}ClFN503$: Calcd: C, 64.86; H, 5.09; N, 12.20. Found: C, 63.44; H, 5.09; N, 12.15.

EXAMPLE 6

N-[5-[3-trichloromethylcarbnyl]-[5H-pyrrolo-[2,1-c]-[1,4]-benzdiazalin-10(11H)-yl carbonyl]-2-chloronhenyl]-2-henylbenzamide To a stirred solution of 2-phenyl-N-[4-(5H-pyrrolo[2,1-c][1,4]benzodiazepin-10(11H)-yl-carbonyl]

2-chlorophenyl]-benzamide (5.00g, 9.7 mmol) in dichloromethane (55 ml) under nitrogen, was added N,N-diisopropylethylamine (3.39 ml, 19.4 mmol), followed by trichloroacetyl chloride (3.25 ml, 29.1 mmol) dropwise over 5 minutes. The reaction mixture was allowed to stir overnight at room temperature. The reaction mixture was washed three times with water. The combined water extract were backwashed with dichloromethane, and the organic extract dried and solvent removed to yield crude product (8.05 g). Crystallisation from ethyl acetate-hexane yielded pure product (5.12 g). An analytical sample obtained from recrystallisation had mp 168–170°.

MS (+ESI), m/z: 663 M+.

Analysis for: $C_{34}H_{27}N_3O_5$ Calcd: C, 61.56; H, 3.49; N,: 6.33. Found: C, 61.28; H, 3.22; N,: 6.32.

EXAMPLE 7

10-{4-[(Bipheny-2-carybonyl)-aminol-2-chloro-benzoyl)-10,11-dihydro-5H-benzo[e]pyrrolo[1,2-a][1,4]-diazepine-3-carboxylic acid To a solution of N-[5-[3-trichloromethycarbonyl]-[5H-pyrrolo-[2,1-c]-[1,4]-benzodiazapin-10(11H)-yl]carbonyl-2-chlorophenyl]-2-phenylbenzamide (2.24g, 3.4 mmol) in acetone (22 ml) was added aqueous sodium hydroxide (2.48 ml, 2.5N, 6.2 mmol) and the reaction stirred at room temperature for 1.25 hours. The reaction was acidified with HCl (3.47 ml, 2N) and the solvent was removed under vacuum. The residue was partitioned between ethyl acetate-water, dried and the solvent was removed to yield crude product (2.41 g). Tritutration with ether-hexane yielded a solid (1.9g). A sample was crystallised from chloroform-methanol-ether mp 216–218. MS (+FAB), m/z: 562/564 (M+H)+.

Analysis for: $C_{34}H_{27}N_3O_5$ Calcd: C, 70.52; H, 4.30; N, 7.48. Found: C, 69.25; H, 4.39; N, 7.14.

EXAMPLE 8

10-(4-[(Biphenyl-2-carbonyl)-amino]-2-chloro-benzoyl)-10,11-dihydro-5H-benzo[e]pyrrolo[1,2-a[1,4]diazepine-3-carboxylic acid-1,1-dimethylhydrazide To a suspension of of N-[5-[3-trichloromethycarbonyl]-[5H-pyrrolo-[2,1-c]-[1,4]-benzodiazapin-10(11H)-yl]carbonyl-2-chlorophenyl]-2-phenylbenzamide (0.941 g, 1.5 mmol) in dichloromethane (2 ml) was added 1,1-dimethylhydrazine (1.1 ml, 15 mmol) and the reaction stirtred for 24 hours. The solid went into solution and later turned to a suspension. The solvent was evaporated and the excess hydrazine removed in vacuo. The residue was purified using silica gel column chromatography in methanol-ethyl acetate (1:20) and product eluted with the same solvent to yield 0.8 g of compound. Two crystallisations from methanol-ether gave 0.454 g of pure product mp 173–176. MS (+FAB), m/z: 604 (M+H)+.

Analysis for: $C_{34}H_{27}N_3O_5$ Calcd: C, 69.59; H, 5.01; N, 11.59. Found: C, 69.40; H, 5.01; N, 11.60.

EXAMPLE 9

10-(4-[(Biphenyl-2-carbonyl)-aminol]2-chloro-benzoyl)-10,11-dihydro-5H-benzo[e]pyrrolo[1,2-a[1,4]diazepine-3-carboxylic acid-piperazine-N-methyl amide Method A A suspension of the carboxylic acid (Example 7) (4 g, 7.12 mmol) in dichloromethane (27 ml) and dimethylformamide (0.66 ml, 8.54 mmol) was cooled to about 0–5° under nitrogen. Oxalyl chloride (0.75 ml, 8.54 mmol) in dichloromethane (3 ml) was gradually added. The mixture was stirred at room temperature for 1.5 hours. To a solution of N-methylpiperazine (3.2 ml, 28.5 mmol), in dichloromethane (30 ml) containing diisopropylethylamine (7.45 ml, 42.72 mmol) was added the freshly prepared solution of the acid chloride dropwise over about 15 minutes under nitrogen. The reaction was allowed to stirr for 1.5 hours at room temperature. The mixture was diluted with dichloromethane (20 ml) and mixture was washed with water, 5% sodium bicarbonate, and 25% saline. The aqueous extract was backwashed with dichloromethane and the combined organic solution was dried and the solvent removed under vacuum to give crude product (5.8 g). The residue was purified by silica gel column chromatography (140 g) in methanol-ethyl acetate (1:20). The product was eluted with methanol-ethylacetate (1:10) to give pure compound as off white foam. A sample (0.97 g, 1.51 mmol) dissolved in a mixture of methanol-ether (1:1, 6 ml) and methanolic hydrogen chlorde (1N, 2 ml, 1.96mM) was added. After stirring for 45 minutes all the solvent was removed in vacuo. The residue was triturated overnight with ether containing few ml of methanol. The resulting amophous solid was filtered to give the crude hydrochloride salt (0.876 g). A repreciptation from ethanol-ether gave (0.516 g) of the salt. MS (EI) m/z: 604 (M+H)+.

Analysis for: $C_{38}H_{34}$ Cl $N_5O_3$. $HCl.1.5H_2$ O Calcd: C, 64.44; H, 5.22; N, 9.89. Found: C, 64.15; H, 5.39; N, 9.61.

Method B To a suspension of the product of Example 7 (2.0 g, 3.56 mmol) in dichloromethane (150 ml) was added successively N-methyl piperizine (0.414 ml, 3.74 mmol), 1-(3-dimethylaminopropyl)-3-ethylcarbodiimide HCl (0.716 g, 3.74 mmol), and 4-dimethylaminopyridine (cat.). The reaction was stirred at room temperature for 36 hours, diluted with dichloromethane, washed with water, NaOH (1N), brine, and dried (MgSO$_4$). Purification by flash chromatography (silica gel; eluting solvent chloroform-methanol 50:1 then 20:1) gave a white foam (1.55 g).

EXAMPLE 10

10-{4-[(Biphenyl-2-carbonyl)-aminol]2-chloro-benzoyl}-10,11-dihydro-5H-1pyrrolo[2,1-c][1,4]benzodiazepine-3-carboxylic acid (2-dimethylamino-ethyl)-methyl-amide The compound of Example 10 was prepared in the same manner as described in Example 9 Method A except that N-methylpiperazine was replaced by N,N,N'-trimethyethylene-diamine. The title compound was obtained as off white amorphous solid. m.p.100–120°, MS (+FAB), m/z: 646 (M+H)+/.

EXAMPLE 11

Biphenyl-2-carboxylic acid{3-chloro-4-[3-(4-piperidinyl-pilperidine-1-carbonyl)-5H,11H-pyrrolo[2,1-c][1,4]benzodiazepine-10-carbonyl]-phenyl}-amide.

The compound of Example 11 was prepared in the same manner as described in Example 9 Method A except that N-methylpiperazine was replaced by 4 -piperidnyl-piperidine. The title compound was obtained as off white amorphous solid mp 209°–219°. MS (+FAB), m/z: 712/714 (M+H)+.

EXAMPLE 12

Biphenyl-2-carboxylic acid {3-chloro-4-[3-(4-dimethylamino-piperidine-1-carbonyl)-5H,11H-1pyrrolo[2,1-c][1,4]benzodiazeline-10-carbonyl]-phenyl}-amide.

The compound of Example 12 was prepared in the same manner as described in Example 9 Method A except that N-methylpiperazine was replaced by 4-dimethylaminopiperidine. The title compound was obtained as brown amorphous solid. m.p.138°–152°. MS (+FAB), rn/z: 672 (M+H)⁺.

Analysis for: $C_{40}H_{38}$, Cl $N_5O_3$. HCl.$H_2O$ Calcd: C, 66.04; H, 5.64; N, 9.63. Found: C, 65.22; H, 5.49; N,9.32.

EXAMPLE 13

Bilphenyl-2-carboxylic acid{3-chloro-4-[3-(4-methyl-piperazine-1 aminocarbonyl)-5H,11H-pyrrolo[2,1-c][1,4]benzodiazepine-10-carbonyl]-phenyl}-amide.

The compound of Example 13 was prepared in the same manner as described in Example 9 Method A except that dimethylhydrazine was replaced by 4-N-methyl-N-amino piperazine. The title compound was obtained as pale yellow solid. m.p.172°–182°, MS (+FAB), n/z: 660 (M+H)⁺.

EXAMPLE 14

10-{4-[(Biphenyl-2-carbonyl)-aminol]2-chloro-benzoyl}-10,11-dihydro-5H-pyrrolo[2,1-c][1,4] benzodiazepine-3-carboxylic acid (2-dimetpyiamino-ethyl) -amide The compound of Example 14 was prepared in the same manner as described in Example 9 Method A except that N-methylpiperazine was replaced by N,N-dimethyl-ethylene-diamine. The title compound was obtained as a white solid m.p. 85–94. MS (+FAB) m/z: 632 (M+H)⁺.

Analysis for: $C_{37}H_{34}ClN_5O_3$. 2 $H_2O$ Calcd: C, 66.45; H, 5.69; N, 10.47. Found: C, 64.57; H, 5.50; N, 9.28.

EXAMPLE 15

Biphenyl-2-carboxylic acid{3-chloro-4-[3-(4-morpholino-1piperidine-1-carbonyl)-5H,11H-pyrrolo[2,1-c][1,4]benzodiazepine-10-carbonyl]-phenyl}-amide.

The compound of Example 15 was prepared in the same manner as described in Example 9 Method A except that N-methylpiperazine was replaced by 4-morpholino-piperidine. The tide compound was obtained as amorphous solid. MS (+FAB), m/z: 714 (M+H)⁺.

EXAMPLE 16

10-(4-[(Biphenyl-2-carbonyl)-aminol]2-methoxv-benzoyl)-10,11-dihydro-5H-benzo[e]pyrrolo[1,2-a[1,4] diazepine-3-carboxylic acid piperazine-N-methyl amide Step a) 2-Methoxy-4-nitrobenzoic acid methyl ester Thionyl chloride (13.9 ml, 190 mrnol) was added, via syringe, to a solution of 4-nitro-2-methoxybenzoic acid (50 g, 250 mmol) and methanol which was stirred at room temperature. The reaction was stirred at room temperature for 16 hours. The volatiles were removed in vacuo. The residue dissolved in dichloromethane, washed with (1) sodium hydroxide, and the organic layer separated and dried (MgSO₄). Evaporation in vacuo gave a light yellow solid (50 g) mp 80–81° C., which was taken directly to the next step.

Analysis for: $C_9H_9NO_5$ Calcd: C, 51.19; H, 4.30; N, 6.63. Found: C, 50.97; H, 4.11; N, 6.51.

Step b) 4-Amino-2-methoxy-benzoic acid methyl ester

A mixture of 2-methoxy-4-nitrobenzoic acid methyl ester (12 g, 57 mmol), palladium (10% on activated carbon), and ethanol (150 ml) was shaken at room temperature under 50 psi of hydrogen for 2 hours. The reaction was filtered through diatomaceous earth, and the diatomaceous earth washed with chloroform. Evaporation of the chloroform washings gave a yellow solid. Purification by crystallization gave a light yellow crystalline solid (8.76 g) mp 148–149° C.

Analysis for: $C_9H_{11}NO_3$ Calcd: C, 59.66; H, 6.12; N, 7.73. Found: C, 59.42; H, 6.02; N, 7.69.

Step c) 4-[(Biphenyl-2-carbonyl)-amino]-2-methoxy-benzoic acid methyl ester

Into a refluxing solution of 2-biphenylcarboxylic acid (9.2 g, 46 mmol) in dichloromethane was added dimethylformamide (0.1 ml, 1.4 mmol) and then neat oxalyl chloride (8.1 ml, 92 mmol) via syringe. The reaction was refluxed for 10 minutes, then the volatiles removed in vacuo. The residue was redissolved in dichloromethane, concentrated and dried under high vacuum for 15 minutes. The acid chloride was dissolved in dichloromethane (50 ml) and added into a 0° C. solution of 4-amino-2-methoxy-benzoic acid methyl ester (8.4 g, 46 mmol), diisopropyl ethylamine (10.5 ml, 60 mmol) and dichloromethane (200 ml). The reaction was warmed to room temperature and stirred for 16 hours. The reaction was diluted with dichloromethane, washed with water, (1N) sodium hydroxide (1) hydrochloric acid, and brine, and dried (MgSO₄). Evaporation gave a yellow foam, which was crystallized from methanol to give a light yellow solid (16.08 g) m.p. 141–142° C.

Analysis for: $C_{22}H_{19}N\ O_4$ Calcd: C, 73.12; H, 5.30; N, 3.88. Found: C, 72.93; H, 5.20; N, 3.83.

Step d) 4-[(Biphenyl-2-carbonyl)-amino]-2-methoxy-benzoic acid Sodium hydroxide (1) (38 ml, 38 mmol) was added to a refluxing solution of 4-[(biphenyl-2-carbonyl)-amino]-2-methoxy-benzoic acid methyl ester (11.6 g, 32 rmmol) in methanol (200 ml). The reaction was refluxed for 2 hours. The volatiles were removed in vacuo and the residue taken into ethyl acetate/HCl (aq). The aqueous layer was re-extracted with ethyl acetate, and the organic extracts combined and dried (MgSO₄). Evaporation gave a pale orange foam, which was crystallized from methanol to give a white solid (9.33 g) mp 158–159° C.

Analysis for: $C_2H_{17}N\ O_4$ Calcd: C, 72.61; H, 4.93; N, 4.03. Found: C, 72.20; H, 4.61; N, 3.96.

Step e) [3-Methoxy-4-(5H,11H-pyrrolo[2,1-c][1,4] benzodiazepine-10-carbonyl)-phenyl]-biphenyl-2-carboxylic acid -amide Into a refluxing solution of 4-[(biphenyl-2-carbonyl)-amino]-2-methoxy-benzoic acid (3.29 g, 9.5 mmol) and dichloromethane (50 ml) was added dimethylformamide (0.02 ml, 0.28 imnol) and then neat oxalyl chloride (0.87 ml, 10 mmol) via syringe. The reaction was refluxed for 10 minutes and then the volatiles were removed in vacuo. The residue was evaporated with fresh dichloromethane and then dried under high vacuum for 15 minutes. The acid chloride was dissolved in dichloromethane (50 ml) and added to a 0° C. solution of 10,1 1-dihydro-5H-pyrrolo[2,1-c][1,4] benzodiazepine (1.57 g, 8.55 mmol), N,N-diisopropylethylamine (1.93 ml, 12.35 mmol) and dichloromethane (200 ml). The reaction was warmed to room temperature and stirred for 2 hours. The reaction mixture was diluted with dichloromethane, washed with water, (1) sodium hydroxide, (1N) hydrochloric acid, and brine, and dried (MgSO₄). Evaporation gave a yellow foam, which was crystallized from methanol to give a white solid (2.05 g) mp 224–226° C.

Analysis for: $C_{33}H_{27}N_3O_3$. Calcd: C, 76.87; H, 5.35; N, 8.07. Found: C, 76.82; H, 5.23; N, 8.04.

Step f) N-[5-[3-trichloromethylcarbonyl]-[5H-pyrrolo-[2,1-c]-[1,4]-benzdiazapin-10(11H)-yl]carbonyl]-2-methoxyphenyl]-2-phenylbenzamide To a solution of the product of Step e from Example 357 (2.5 g, 4.87 mmol) in dichloromethane (50 ml) at 0° C. was added trichloroacetyl chloride (1.09 ml, 9.74 mmol) via syringe, and the reaction was stirred at room temperature for 4 hours. The reaction was diluted with dichloromethane, washed with sodium bicarbonate and brine, and the organic extracts were dried ($MgSO_4$). Evaporation and filtration of the residue through a silica gel pad followed by washing with ethyl acetate/ hexane 1/1, gave the desired product as a white foam (1.5 g) m.p. 139–143° C.

Analysis for: $C_{35}H_{26}Cl_3N_3O_4+0.25\ H_2O$. Calcd: C,63.36; H,4.03; N,6.33. Found: C,63.05; H,4.03; N,6.21.

Step g) 10-{4-[(Bipheny-2-carbonyl)-amino]-2-methoxybenzoyl)-10,11-dihydro-5H-benzo[e]pyrrolo[1,2-a][1,4] diazepine-3-carboxylic acid Sodium hydroxide (1) (2.0 ml, 1.92 mmol) was added to a room temperature solution of N-[5-[3-trichloromethylcarbnyl]-[5H-pyrrolo-[2,1-c]-[1,4]-benzdiazapin- 10(1 1H)-yl]carbonyl]-2-methoxyphenyl]-2-phenylbenzamide (0.8 g, 1.2 mmol) in tetrahydrofuran (10 ml), and the reaction stirred for 1.5 hours. Hydrochloric acid (1N) was added and the reaction was diluted with ice. The volatiles were removed in vacuo and the white solid was filtered and dried to give (0.8 g) of the titled compound mp 149–151° C.

Analysis for: $C_{34}H_{27}N_3O_5$ Calcd: C,70.21; H,5.14; N, 7.22. Found: C,70.20; H,4.89; N, 7.31.

Step h) 10-(4-[(Biphenyl-2-carbonyl)-amino]-2-methoxy-benzoyl)-10, 11-dihydro-5H-benzo[e]pyrrolo[1,2-a[1,4] diazepine-3-carboxylic acid-piperazine-N-methyl-amide A solution of 10-{4-[(bipheny-2-carbonyl)-amino]-2-methoxybenzoyl)-10,11-dihydro-5H-benzo[e]pyrrolo[1,2-a][1,4] diazepine-3-carboxylic acid (0.434 g, 0.778 mmol), 1-(3-dimethylaminopropyl)-3-ethylcarbodiimide hydrochloride (0.157 g, 0.817 mmol), 4-dimethylaminopyridine (cat.), and N-methyl piperazine (.091 ml, 0.817 mmol) in dichloromethane was stirred at room temperature for 3.5 hours. The reaction was diluted with dichloromethane, and washed with water and brine. The organic extracts were dried ($MgSO_4$) and concentrated to give a white foam. Purification by flash chromatography (silica gel; eluting solvent chloroform-methanol 50:1 then 20:1) and crystallization from ethanol gave a white solid (0.23 g) m.p. 139°–140° C.

Analysis for: $C_{39}H_{37}N_5O_4+1.0H_2O$ Calcd: C, 71.21; H, 5.98; N, 10.65. Found: C, 71.25; H, 5.99; N, 10.64.

EXAMPLE 17

10-(4-[(Biphenyl-2-carbonyl)-amino]-2-methoxy-benzoyl)-10,11-dihydro-5H-benzo[e]pyrrolo[1,2-a[1, 4]diazepine-3-carboxylic acid-1,1-dimethylhydrazide To a solution of the product of Step h from Example 16 (1.0 g, 1.947 mmol) in dichloromethane (20 ml) at 0° C. was added trichloroacetyl chloride (0.434 ml, 3.89 mmol) via syringe, and the reaction was stirred at room temperature for 4 hours. The reaction was diluted with dichloromethane, washed with sodium bicarbonate and brine, and the organic extracts dried ($MgSO_4$). Evaporation and filtration of the residue through a silica gel pad, washing with ethyl acetate-hexane 1:1, gave the trichloroketone as a white foam when concentrated. The foam was dissolved in neat N,N-dimethylhydrazine at room temperature, and then heated at reflux for 25 minutes. The volatiles were removed in vacuo, and the residue adsorbed onto silica gel and purified by flash chromatography (eluting solvent ethyl acetate-hexane 1:1 then ethyl acetate-methanol 4:1). Crystallization from ethanol gave a tan solid (0.23 g) m.p. 164°–165° C.

Analysis for: $C_{36}H_{33}N_5O_4+1.0H_2O$ Calcd: C, 70.0; H, 5.71; N, 11.34. Found: C, 70.01; H, 5.62; N, 11.29.

EXAMPLE 18

10-{4-[(Biphenyl-2-carbonyl)-amino]2-chloro-benzoyl}-10,11-dihydro-5H-pyrrolo[2,1-c][1,4] benzodiazepine-3-carboxylic acid (glycyl)- amide The compound of Example 18 was prepared in the same manner as described in Example 8, except that dimethylhydrazine was replaced by t-butyl glycine as the reactant. The resulting t-butyl ester (0.725 g) of the title compound thus obtained was hydrolysed by treatment with formic acid (2.3 ml) at room temperature for 48 hours to yield the title compound as white amorphous solid mp.176–186. MS (ESI) m/z 617 (M–H)$^+$.

Analysis for: $C_{36}H_{30}N_4O_6$ Calcd: C: 67.9, H:4.40, N: 9.05. Found C: 66.51, H: 4.23, N:8.44.

EXAMPLE 19

10-[2-Chloro-4-(2-thiophen-2-yl-benzoylamino)-benzoyl]-10,11-dihydro-5H-2pyrrolo[2,1-c][1,4,4] benzodiazepine-3-carboxylic acid-1,1-dimethyl hydrazide N-[3Chloro-4-(5H,11H-pyrrolo[2,1-c][1,4]benzodiazepine-10-carbonyl)-phenyl]-2-thiophen-2-yl-benzamide Step a) 2-Bromobenzoyl chloride To a solution of bromobenzoic acid (1.88 g, 9.35 mmol) in anhydrous tetrahydrofuran (20 ml), under nitrogen, was added 1 drop of dimethylformamide followed by addition of oxalyl chloride (1 ml, 11.4 mmol). The mixture was stirred at room temperature until gas evolution ceased and then heated to reflux. The solution was cooled to ambient temperature before being concentrated in vacuo to produce a gold oil (1.87 g) which was used without further purification.

Step b) 2-Bromo-N-[3-chloro-4-(10,11-dihydro-5H-pyrrolo[2,1-c][1,4]benzodiazepine-10-carbonyl)-phenyl]-benzamide To a stirred solution of 10,11-dihydro-10-(2-chloro-4-aminobenzoyl)-5H-pyrrolo[2,1-c][1,4]benzodiazepine (2.25 g. 6.66 mnmol) in dichloromethane (40 ml), under nitrogen, was added triethylamine (1.19 ml, 8.53 mmol). The mixture was cooled to 0° C. before a solution of 2-bromobenzoyl chloride (1.87 g, 8.52 mmol) in dichloromethane (20 ml) was added dropwise. The cooling bath was removed and stirring was continued for 14 hours. The reaction mixture was poured into water. The organic layer was separated and sequentially washed with water, saturated aqueous sodium bicarbonate, and water before being dried ($Na_2SO_4$). The material was filtered and concentrated in vacuo to yield a pale orange foam (2.00 g). Purification by flash chromatography on silica gel with hexane-ethyl acetate (1:1) as the mobile phase resulted in a white powder (1.39 g), m.p. 188°–189° C. MS (EI),m/z; 519 (M$^+$).

Analysis for: $C_{26}H_{19}BrClN_3O_2+0.5H_2O$ Calcd: C, 58.93; H, 3.80; N, 7.93 Found: C, 59.12; H, 3.62; N, 7.75

Step c) N-[3-Chloro-4-(5H,11H-pyrrolo[2,1-c][1,4] benzo-diazepine-10-carbonyl)-phenyl]-2-thiophen-2-yl-benzamide The 2-bromo-N-[3-chloro-4-(10,11-dihydro-5H-pyrrolo [2,1-c] [1,4]benzo-diazepine-10-carbonyl)-phenyl]-benzamide (1.04 g, 2.0 mmol), thiophene-2-boronic acid (0.32 g, 2.4 mmol), and barium hydroxide octahydrate (0.88 g, 2.8 mmol) were suspended in ethylene glycol dimethyl ether (28.8 ml) and water (4.8 ml). The heterogeneous mixture was stirred at ambient temperature and purged with nitrogen for ten minutes before bis(triphenylphosphine) palladium (II) chloride (0.17 g, 0.24 mmol) was added and the reaction was placed under a static pressure of nitrogen. The reaction was heated in an oil bath at 70° C. After 20 hours, additional thiophene-2-boronic acid (0.13 g, 1 mmol) was added to the reaction. After 24 hours of total reaction time, additional bis(triphenylphosphine)-palladium(II) chloride (84 mg, 0.12 mmol) was added to the reaction flask. The reaction was cooled to room temperature and the mixture was extracted into benzene. The combined organic extracts were washed with brine, dried ($MgSO_4$), filtered and concentrated in vacuo to yield a brown solid (1.42 g). The solid was triturated with ethyl acetate and filtered. The filtrate was purified by flash chromatography using silica gel with hexane-ethyl acetate (1:1) as the mobile phase to afford a pale yellow solid which was dried under vacuum at 78° C. for two days (0.59 g), m.p. 132°–136° C. MS (EI),m/z: 523 ($M^+$).

Analysis for: $C_{30}H_{22}ClN_3O_2S+0.5H_2O$ Calcd: C, 67.53; H, 4.36; N, 7.88 Found: C, 67.53; H, 4.08; N, 7.90

Step d) N-{3-Chloro-4-[3-(trichlorocarbonyl)-(5H,11H-pyrrolo-[2,1-c][1,4]benzodiazepine-10-carbonyl]-phenyl}-2-thiophen-2-yl-benzamide The product of step C was converted to the corresponding trichloroketone according to the protocol outlined in step A of Example 1.

Step e) 10-[2-Chloro-4-(5-thiophen-2-yl-benzoylamino)-benzoyl]-10,11-dihydro-5H-pyrrolo[2,1-c][1,4]benzodiazepine-3-carboxylic acid The trichloroketone prepared in step D was hydrolyzed to the title acid according to the protocol outlined in step B of Example 1

Step f) 10-[2-Chloro-4-(2-thiophen-2-yl-benzoylamino)-benzoyl]-10,11-dihydro-5H-pyrrolo[2,1-c][1,4]benzodiazepine-3-carboxylic acid-1,1-dimethylhydrazide The trichloroketone prepared in step D reacted with N,N dimethyl hydrazine according to the protocol in Example 8.

EXAMPLE 20

10-[2-Chloro-4-(3-pyridin-2-yl-benzoylamino)-benzoyl]-10,11-dihydro-5H-pyrrolo[2,1-c][1,4]benzodiazelpine-3-carboxylic acid-pilperazine-N-methyl amide N-[3-Chloro-4-(5H,11H-pyrrolo[2,1-c][1,4]benzodiazepine-10-carbonyl)-phenyl]-3-pyridin-2-yl-benzamide Step a) The compound of Example 20a was prepared in the same manner as described in Example 19 following the steps 19a, 19b. In Step 19a, 2-(pyridin-3-yl)-benzoic acid was substituted for 2-bromobenzoic acid. Preparation of 2-(pyridin-3-yl)-benzoic acid was carried out in the manner of Timari, et al (Chem. Ber. 1992, 125, 929) substituting 3-bromopyridine in place of 2-bromopyridine. The title compound was obtained as an off-white powder (0.21 g) m.p. 155°–158° C.

Analysis for: $C_{31}H_{23}ClN_4O_2+0.85H_2O$ Calcd: C, 69.68; H, 4.66; N, 10.49 Found: C, 69.69; H, 4.70; N, 10.16

N-{3-Chloro-4-[3-(trichlorocarbonyl)-(5H,11H-pyrrolo[2,1-c][1,4]-benzodiazepine-10-carbonyl)-phenyl}-3-pyridin-2-yl-benzamide Step b) The product of step A was converted to the corresponding trichloro-ketone according to the protocol outlined in step A of Example 1.

10-[2-Chloro-4-(3-pyridin-2-yl-benzoylamino)-benzoyl]-10,11-dihydro-5H-pyrrolo[2,1-c][1,4]benzodiazepine-3-carboxylic acid Step c) The trichloroketone prepared in step B was hydrolyzed to the title acid according to the protocol outlined in step B of Example 1.

10-[2-Chloro-4-(3-pyridin-2-yl-benzoylamino)-benzoyl]-10,11-dihydro-5H-pyrrolo[2,1-c][1,4]benzodiazepine-3-carboxylic acid-piperazine-N-methyl amide Step d) The acid prepared in step C was converted into an amide using method A of Example 9.

EXAMPLE 21

10-[2-Chloro-4-(4-pyridin-2-yl-benzoylamino)-benzoyl]-10,11-dihydro-5H-pyrrolo[2,1-c][1,4]benzodiazepine-3-carboxylic acid (2-dimethylamino-ethyl)-methyl-amide N-[3-Chloro-4-(5H,11H-pyrrolo[2,1-c][1,4]benzodiazepine-10-carbonyl)-phenyl]-2-pyridin-4-yl-benzamide Step a) The compound of Example 21a was prepared in the same manner as described in Example 19 following steps 19a and 19b. In Step 19a, 2-(pyridin-4-yl)-benzoic acid was substituted for 2-bromobenzoic acid. Preparation of 2-(pyridin-4yl)-benzoic acid was carried out in the manner of Timari, et al (Chem. Ber. 1992, 125, 929) substituting 4-bromopyridine hydrochloride and an additional equivalent of base in place of 2-bromopyridine. The title compound was obtained as a pale yellow solid (1.21 g) m.p. 165°–168° C.

Analysis for: $C_{31}H_{23}ClN_4O_2+0.47H_2O$ Calcd: C, 70.59; H, 4.57; N, 10.62 Found: C, 70.58; H, 4.50; N, 10.33

N-{3-Chloro-4-[3-(trichlorocarbonyl)-(5H,11H-pyrrolo[2,1-c][1,4]benzo-diazepine-10-carbonyl)-phenyl}-2-pyridin-4-yl-benzamide Step b) The product of step A was converted to the corresponding trichloroketone according to the protocol outlined in step A of Example 1.

10-[2-Chloro-4-(4-pyridin-2-yl-benzoylamino)-benzoyl]-10,11-dihydro-5H-pyrrolo[2,1-c][1,4]benzodiazepine-3-carboxylic acid Step c) The trichloroketone prepared in step B was hydrolyzed to the title acid according to the protocol outlined in step B of Example 1.

10-[2-Chloro-4-(4-pyridin-2-yl-benzoylamino)-benzoyl]-10,11-dihydro-5H-pyrrolo[2,1-c][1,4]benzodiazepine-3-carboxylic acid (2-dimethylaminoethyl)-methyl-amide Step d) The acid prepared in step c was converted into its 2- dimethyl amino-ethyl-methyl amide according to the protocol in example 10

EXAMPLE 22

10-[2-Chloro-4-(2-pyridin-2-yl-benzoylamino)-benzoyl]-10,11-dihydro-5H-pyrrolo[2,1-c][1,4]benzodiazepine-3-carboxylic acid-piperazine-N-methyl amide N-[4-(3-Methoxy-5H,11H-pyrrolo[2,1-c][1,4]benzodiazepine-10-carbonyl)-phenyl]-2-pyridin-2-yl-benzamide Step a) 2-Methoxy-4-[(2-pyridin-2-ylbenzoyl)amino]benzoyl chloride To a solution of 2-methoxy-4-[(2-pyridin-2-ylbenzoyl)amino]benzoic acid (0.92 g, 2.64 mmol) in anhydrous tetrahydrofuran (25 ml), under nitrogen, was added 1 drop of dimethylformamide followed by addition of oxalyl chloride (0.28 ml, 3.17 mmol). The mixture was stirred at room temperature until gas evolution ceased. The solution was concentrated in vacuo to produce a tan solid (1.16 g) which was used without further purification.

Step b) N-[4-(3-Methoxy-5H,11H-pyrrolo[2,1-c][1,4]benzodiazepine-10-carbonyl)-phenyl]-2-pyridin-2-yl-benzamide To a stirred solution of 10,11-dihydro-5H-pyrrolo[2,1-c][1,4]benzodiazepine (0.405 g. 2.20 mmol) in dichloromethane (30 ml), under nitrogen, was added triethylamine (0.37 ml, 2.64 mmol). The mixture was cooled to 0° C. and a solution of the crude 2-methoxy-4-[(2-pyridin-2-ylbenzoyl)amino]benzoyl chloride (1.16 g) in dichloromethane (30 ml) was added dropwise. After 5 hours the reaction mixture was poured into water. The organic layer was separated and sequentially washed twice with water and aqueous sodium bicarbonate, and once with water and dried ($Na_2SO_4$). The material was filtered and concentrated in vacuo to yield a marron solid (1.1 g). Purification by flash chromatography on silica gel with hexane-ethyl acetate-methlyene chloride, methanol (3:6:2:0.5) as a mobile phase, followed by concentration under vacuum, resulted in a pale purple solid (0.88 g), m.p. 138°–140° C. MS (FAB),m/z: 515 (M+H).

Analysis for: $C_{32}H_{26}N_4O_3$+0.43$H_2O$ Calcd: C, 73.58; H, 5.18; N, 10.73. Found: C, 73.59; H, 5.05; N, 10.47.

N-{3-Chloro-4-[3-(trichlorocarbonyl)-(5H,11H-pyrrolo[2,1-c][1,4]-benzodiazepine-10-carbonyl)-phenyl}-2-pyridin-2-yl-benzamide Step c) The product of step B was converted to the corresponding trichloroketone according to the protocol outlined in step A of Example 1.

10-[2-Chloro-4-(2-pyridin-2-yl-benzoylamino)-benzoyl]-10,11-dihydro-5H-pyrrolo[2,1-c][1,4]benzodiazepine-3-carboxylic acid Step d) The trichloroketone prepared in step C was hydrolyzed to the title acid according to the protocol outlined in step B of Example 1.

10-[2-Chloro-4-(2- pyridin-2-yl-benzoylamino)-benzoyl]-10,11-dihydro-5H-pyrrolo[2,1-c][1,4]benzodiazepine-3-carboxylic acid-piperazine-N-methyl amide Step d) The acid prepared in step D was converted to its N-methyl piperazine amide via Method B in Example 9

EXAMPLE 23

10-[2-Bromo-4-(2-pyridin-2-yl-benzoylamino)-benzoyl]-10,11-dihldro-5H-pyrrolo[2,1-c][1,4]benzodiazepine-3-carboxylic acid-1,1-dimethylhydrazide N-[3-Bromo-4-(5H,11H-pyrrolo[2,1-c][1,4]benzodiazepine-10-carbonyl)-phenyl]-2-pyridin-2-yl-benzamide Step a) Methyl 2-bromo-4-aminobenzoate A solution of 2-(pyridin-2-yl)benzoic acid (2.85 g, 14.3 mmol) in dry tetrahydrofuran (20 ml) was treated with 1 drop of dimethylformamide followed by oxalyl chloride (1.5 ml, 17.1 mmol) in dry tetrahydrofuran (5 ml). When the gas evolution stopped the mixture was warmed to reflux for 5 minutes cooled to room temperature and concentrated in vacuo to a bright yellow solid. The solid was slurried with tetrahydrofuran (20 ml) and concentrated again. The crude acid chloride was used in the next step without further purification.

Step b) Methyl 2-Bromo-4-[(2-pyridin-2-yl-benzoyl) amino]benzoate

A solution of methyl 2-bromo-4-amino benzoate (3 g, 13 mmol) and triethylamine (2.5 ml, 18 mmol) in dichloromethane (50 ml) was cooled to 0° and was treated with a slurry of 2-(pyridin-2-yl)benzoyl chloride in dichloromethane (20 ml). Stirring at room temperature was maintained for 4 hours. The reaction was quenched with 20% acetic acid, wash sequentially with saturated aqueous sodium bicarbonate, water then saturated brine solution. The solution was dried (MgSO4), filtered and concentrated in vacuo to give 5.23 g of a white foam. MS (+FAB) m/z 411/413 (M+H)+.

Analysis for: C20H15BrN2O3 Calcd: C, 58.41; H, 3.68; N, 6.81. Found: C, 57.73; H, 3.66; N, 6.54.

Step c) 2-Bromo-4-[(2-pyridin-2-yl-benzoyl)amino] benzoic acid

A solution of methyl 2-bromo-4-[(2-pyridin-2-yl-benzoyl)amino]benzoate in methanol (100 ml) was treated with 1N sodium hydroxide (15 ml, 1.2 eq). The solution was warmed to reflux for 3.5 hours and additional 1N sodium hydroxide was added (10.4 ml., 2 eq total). Reflux was maintained for 2 additional hours and the reaction was stirred at room temperature overnight. The sample was concentrated in vacuo to a syrup and diluted with water. The aqueous solution was washed with ethyl acetate and the aqueous layer was adjusted to a pH of 4.5–5 with acetic acid. The product was precipitated, filtered and air dried to give a tan solid (4.43 g). MS (EI) rD/z: 397/399 (M+).

Step d) 2-Bromo-4-[(2-pyridin-2-yl-benzoyl)amino] benzoyl chloride

To a solution of 2-bromo-4-[(2-pyridin-2-yl-benzoyl)amino]benzoic acid (1.4 g, 3.52 mmol) in anhydrous tetrahydrofuran (25 ml), under nitrogen, was added 1 drop of dimethylformamide followed by the addition of oxalyl chloride (0.37 ml, 4.23 mmol). The mixture was stirred at room temperature until there was no further evolution of gas and then heated to reflux. The reaction mixture was cooled to ambient temperature and concentrated in vacuo to produce a tan solid (1.385 g) which was used without further purification.

Step e) N-[3-Bromo-4-(5H,11H-pyrrolo[2,1-c][1,4]benzodiazepine-10-carbonyl)-phenyl]-2-pyridin-2-yl-benzamide To a stirred solution of 10,11-dihydro-5H-pyrrolo[2,1-c][1,4]benzodiazepine (0.54 g. 2.93 mmol) in dichloromethane (35 ml), under nitrogen, was added triethylamine (0.49 ml, 3.52 mmol). The mixture was cooled to 0° C. before a suspension of the crude 2-methoxy-4-[(2-pyridin-2-ylbenzoyl)-amino]benzoyl chloride (1.4 g) in dichloromethane (5 ml) was added dropwise. After the addition was complete, the reaction mixture was allowed to warm to room temperature. After 18 hours the reaction mixture was poured into water and sequentially washed with water, saturated aqueous sodium bicarbonate, twice with 10% aqueous acetic acid, once with saturated aqueous sodium bicarbonate and once with water. The organic solution was dried ($Na_2SO_4$), filtered and concentrated in vacuo to yield a dark purple foam (1.73 g). Purification by flash chromatography on silica gel with hexane-ethyl acetate (1:2) as the mobile phase, followed by concentration in vacuo, resulted in a white solid (1.23 g), m.p. 227.5°–229° C. MS (ESI),m/z: 563 (M+).

Analysis for: $C_{31}H_{23}BrN_4O_2$ Calcd: C, 66.08; H, 4.11; N, 9.94 Found: C, 65.84; H, 3.86; N, 9.85

N-{3-Bromo-4-[3-(trichlorocarbonyl)-(5H,11H-pyrrolo[2,1-c][1,4]-benzodiazepine-10-carbonyl)-phenyl}-2-pyridin-2-yl-benzamide Step f) The product of step E was converted to the corresponding trichloroketone according to the protocol outlined in step A of Example 1.

10-[2-Bromo-4-(2-pyridin-2-yl-benzoylamino)-benzoyl]-10,11-dihydro-5H-pyrrolo[2,1-c][1,4]benzodiazepine-3-carboxylic acid Step g) The trichloroketone prepared in step F was hydrolyzed to the title acid according to the protocol outlined in step B of Example 1.

10-[2-Bromo-4-(2-pyridin-2-yl-benzoylamino)-benzoyl]-10,11-dihydro-5H-pyrrolo[2,1-c][1,4]benzodiazepine-3-carboxylic acid 1,1-dimethylhydrazide Step h) The trichloroketone prepared in step F was treated with 1,1 dimethyl hydrazine according to the protocol outlined in Example 8.

EXAMPLE 24

10-[2-Chloro-4-(8-quinoloinylylamino)-benzoyl]-10,11-dihydro-5H-pyrrolo[2,1-c][1,4]benzodiazepine-3-carboxylic acid-piperazine-N-methyl amide Quinoline-8-carboxylic acid [4-(5H,11H-pyrrolo[2,1-c][1,4]-benzodiazepine-10-carbonyl)-3 chloro-phenyl]-amide Step a) The compound of Example 24 was prepared in the same manner described in Example 19 Steps 19a and 19b. In Step 19a, quinoline-8-carboxylic acid was substituted for 2-bromobenzoic acid. The title compound was obtained as a white powder (0.69 g) m.p. 230°–231° C.

Analysis for: $C_{29}H_{21}ClN_4O_2$+0.33$H_2O$ Calcd: C, 69.81; H, 4.38; N, 11.23 Found: C, 69.81; H, 4.09; N, 11.14

Quinoline-8-carboxylic acid-4-[3-(trichlorocarbonyl)(5H,11H-pyrrolo[2,1-c][1,4]benzodiazepine-10-carbonyl)-3 chloro-phenyl]-amide Step b) The product of step A was converted to the corresponding trichloro-ketone according to the protocol outlined in step a of Example 1.

10-[2-Chloro-4-(8-quinolincarboxamido)-benzoyl]-10,11-dihydro-5H-pyrrolo [2,1-c][1,4]benzodiazepine-3-carboxylic acid Step c) The trichloroketone prepared in step b was hydrolyzed to the title acid according to the protocol outlined in step b of Example 1.

10-[2-Chloro-4-(8-quinolinylamino)-benzoyl]-10,11-dihydro-5H-pyrrolo [2,1-c][1,4]benzodiazepine-3-carboxylic acid -piperazine-N-methyl amide Step d) The acid prepared in step c was converted into its N-methyl piperazine amide using method B of Example 9.

EXAMPLE 25

2-Phenyl-cyclopent-1-enecarboxylic acid [3-chloro-4-(3-carboxylic acid (2-dimethylamino- ethyl)-methyl-amide -5H,11H-pyrrolo[2,1 c][1,4]-benzodiazepine-10-carbonyl)-phenyl]-amide Step a) [2-Phenyl-cyclopent-1-enecarboxylic acid]

Sodium hydroxide (1N) (10.7 ml, 11.8 mmol) was added to a refluxing solution of 2-phenyl-cyclopent-1-enecarboxylic acid methyl ester (2.32 g, 10.7 mmol) (Lin et al., *J. Chin. Chem. Soc.*, 1993, 40, 273–282) in methanol (40 ml). The reaction was refluxed for 2 hours. The volatiles were removed in vacuo and the residue partitioned between ethyl acetate and (1N) hydrochloric acid. The aqueous layer was re-extracted with ethyl acetate, and the organic extracts combined and dried (MgSO$_4$). Evaporation of the solution in vacuo gave a pale yellow solid, which was recrystallized from acetone/hexane to give a white solid (1.27 g) m.p. 145°–146° C.

Analysis for: $C_{12}H_{12}O_2$ Calcd: C, 76.57; H, 6.43; N, Found: C, 76.47; H, 6.35; N, Step b) 2-phenyl-cyclopent-1-enecarbonyl chloride To solution of 2-phenyl-cyclopent-1-enecarboxylic acid (0.43 g, 2.28 mmol) in dichloromethane (20 ml) was added via syringe dimethylformamide (1 drop) and then neat oxalyl chloride (0.4 ml, 4.56 mmol). The reaction was stirred at room temperature for 2 hours and then the volatiles were removed in vacuo. The residue was redissolved in dichloromethane, concentrated in vacuo and dried under high vacuum for 15 minutes to give an amber oil which was used directly in the next step without further purification.

Step c) 2-Phenyl-cyclopent-1-enecarboxylic acid [4-(5H,11H-pyrrolo-[2,1-c][1,4]benzodiazepine-10-carbonyl)-3-chloro-phenyl]-amide The product from Example 25 step b, 2-phenyl-cyclopent-1-enecarbonyl chloride was dissolved in dichloromethane (20 ml) and added at room temperature to a solution of 10,11-dihydro-10-(2-chloro-4-aminobenzoyl)-5H-pyrrolo [2,1-c][1,4]benzodiazepine (0.77 g, 2.28 mmol, 4-dimethylaminopyridine (cat) in dichloromethane (20 ml). Triethylamine (0.38 ml, 2.74 mmol) was then added via syringe. The reaction was stirred for 16 hours, diluted with dichloromethane and washed with sodium bicarbonate, (1N) hydrochloric acid, and brine. The dichloromethane solution was dried (MgSO$_4$) and concentrated in vacuo to give a yellow solid. Purification by flash chromatography (eluting solvent chloroform/methanol 50/1 and hexane/ethyl acetate 2/1) afforded a white solid (0.70 g) m.p. 121°–122° C.

Analysis for: $C_{31}H_{26}Cl N_3O_2$ Calcd: C, 73.29; H, 5.16; N, 8.27 Found: C, 73.18; H, 5.02; N, 8.11

2-Phenyl-cyclopent-1-enecarboxylic acid [3-chloro-4-(3-trichloro-carbonyl)-5H,11H-pyrrolo[2,1-c][1,4] benzodiazepine-10-carbonyl)-phenyl]-amide Step d) The product of step C was converted to the corresponding trichloroketone according to the protocol outlined in step A of Example 1.

2-Phenyl-cyclopent-1-enecarboxylic acid [3-chloro-4-(3-carboxylic acid-5H,11H-pyrrolo[2,1-c][1,4] benzodiazepine-10-carbonyl)-phenyl]-amide Step e) The trichloroketone prepared in step D was hydrolyzed to the title acid according to the protocol outlined in step B of Example 1.

2-Phenyl-cyclopent-1-enecarboxylic acid [3-chloro-4-(3-carboxylic acid (2-dimethylamino- ethyl)-methyl-amide -5H,11H-pyrrolo[2,1 c][1,4]-benzodiazepine-10-carbonyl)-phenyl]-amide Step f) The amide was prepared by reaction of the acid prepared in step e, above, according to the protocol outlined in Example 10

Effects on the Antagonism of Endogenous Arginine Vasopressin Antidiuretic ($V_2$) Response in Conscious Rats with Free Access to Water Drinking Before but not During the Experiment:

Male or female normotensive Sprague-Dawley rats (Charles River Laboratories, Inc., Kingston, N.Y.) of 400–450 g body weight were supplied with Laboratory Rodent Feed #5001 (PMI Feeds, Inc., Richmond, Ind.) and water ad libitum. On the day of test, rats were placed individually into metabolic cages equipped with stainless steel screens (to separate the feces from the urine) and funnels for collection of urine. Vehicle or reference agent was given at various oral doses. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Mass., 02062). or an Advanced CRYOMATIC Osmometer, Model 3C2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. In the following results, increased urine volume and decreased osmolality relative to AVP-control indicates activity. The results of this test on representative compounds of this invention are shown in Table 5.

Binding to Membranes of Mouse Fibroblast Cell Line (LV-2) Transfected with the cDNA Expressing the Human $V_2$ Vasopressin Receptor Membrane Preparation Flasks of 175 ml capacity, containing attached cells grown to confluence, are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J.) is added and the flasks are left undisturbed for 2 min. The content of all flasks is poured into a centrifuge tube and the cells pelleted at 300×g for 15 min. The Hank's based solution is aspirated off and the cells homogenized with a polytron at setting #6 for 10 sec in 10.0 mM Tris.HCl buffer, pH 7.4 containing 0.25 M sucrose and 1.0 mM EDTA. The homogenate is centrifuged at 1500×g for 10 min to remove ghost membranes. The supernatant fluid is centrifuged at 100,000×g for 60 min to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

Receptor Binding

For binding experiments, the following is added in ml volume to wells of a 96 well format of a microtiter plate: 100.0 ml of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 ml of [$^3$H] Arginine$^8$, vasopressin (S.A. 75.0 Ci/mmole) at 0.8 nM and the reaction initiated by the addition of 80.0 ml of tissue membranes (200.0 mg tissue protein). The plates are left undisturbed on the bench top for 120 min to reach equilibrium. Non specific binding is assessed in the presence of 1.0 mM of unlabeled ligand, added in 20 ml volume. For test compounds, these are solubilized in 50% dimethylsulfoxide (DMSO) and added in 20.0 ml volume to a final incubation volume of 200 ml. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio). The results of this test on representative compounds of this invention are shown in Table 5.

TABLE 5

Rat Urine Volume Data* and Binding Assay to Membranes of Mouse Fibroblast Cell Line (LV-2) Transfected with the cDNA Expressing the Human V2 Receptor

| Example Number | Urine Volume (ml/4 hrs) 10 mg/kg rat p.o. | Vasopressin Binding Human V2 Receptor nM |
|---|---|---|
| Example 1 | 13.2 | 14 |
| Example 2 | 11.5 | |
| Example 3 | 22 | 15 |
| Example 4 | 9.2 | 60 |
| Example 5 | 9.1 | 60 |
| Example 6 | | 5.6 |

TABLE 5-continued

Rat Urine Volume Data* and Binding Assay to Membranes of Mouse Fibroblast Cell Line (LV-2) Transfected with the cDNA Expressing the Human V2 Receptor

| Example Number | Urine Volume (ml/4 hrs) 10 mg/kg rat p.o. | Vasopressin Binding Human V2 Receptor nM |
|---|---|---|
| Example 7 | 19.2 | 4.3 |
| Example 8 | 40.9 | 8.6 |
| Example 9 | 23.7 | 3.3 |
| Example 10 | 22.2 | 5.5 |
| Example 11 | 20.5 | 9.3 |
| Example 12 | 21.4 | |
| Example 13 | 16.8 | |
| Example 14 | 11.3 | |
| Example 15 | 19.3 | 10.7 |
| Example 16 | 24.3 | |
| Example 17 | 9.4 | |
| Example 18 | 7.8 | 7.6 |

*Volume of urine produced in a 4 hour time period by the oral administration of 10 mg/kg dose to rats.

What is claimed:

1. A compound of the formula:

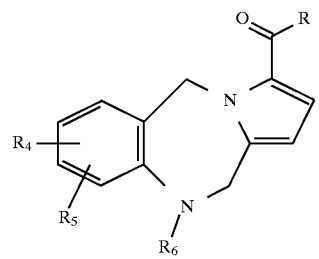

wherein;

R is selected from —OH, —$NR_1R_3$, —$NHOR_1$, —N—$(CH_2)_n$—COOH,

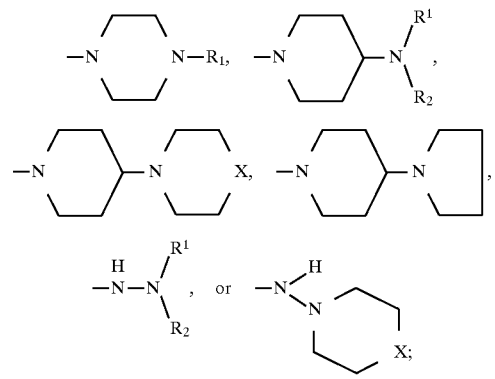

$R_1$ and $R_2$ are, independently, hydrogen or lower alkyl; $R_3$ is

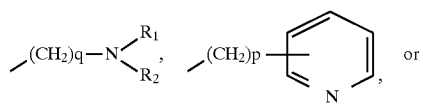

-continued (CH₂)p—[imidazole ring with N]—N;

X is $CH_2$, $NR_1$, O, S;
p is 1 to 4;
q is 2 to 4;
$R_4$ and $R_5$ are, independently, selected from hydrogen, lower alkyl, halogen, amino, cyano, trifluoromethyl, hydroxy, or lower alkoxy;
$R_6$ is a moiety of the formula:

$$-\overset{O}{\underset{\|}{C}}-Ar$$

Ar is a moiety selected from

[pyridine ring with $R_7$, $R_8$, $R_9$] or [benzene ring with $R_7$, $R_8$, $R_9$];

$R_7$ and $R_8$, are independently selected from the group of hydrogen, halogen, cyano, lower alkyl, lower alkoxy, hydroxy, or trifluoromethyl;
$R_9$ is a moiety of the formula:

[three structures with $R_1$, N, O, Ar', $R_{10}$, Ar'']

$R_{10}$ is selected from $C_3$–$C_7$ cycloalkyl, cyclopentenyl, cyclohexenyl, or the moiety

[cyclopentene with Ar'']

Ar' is a moiety selected from

[three aromatic ring structures with Ar'', $R_{11}$, $R_{12}$]

$R_{11}$ and $R_{12}$ are selected independently from hydrogen, F, Cl, Br, cyano, lower alkyl, lower alkoxy, phenoxy, or trifluoromethyl;
Ar'' is selected from:
 a) phenyl;
 b) a five membered aromatic heterocyclic ring having one or two heteroatoms selected from N, O, S;
 c) a five membered aromatic heterocyclic ring having three or four nitrogen atoms; or
 d) a six membered aromatic heterocyclic ring having one, two or three nitrogen atoms;

and Ar'' may be optionally substituted with halogen, lower alkyl, hydroxy, lower alkoxy, or trifluoromethyl;

or a pharmaceutically acceptable salt thereof.

2. A compound of claim 1 having the formula:

[pyrrole-based structure with R, $R_4$, $R_5$, $R_6$]

wherein

R is selected from —OH, —$NR_1R_3$, —N—$(CH_2)_n$—COOH,

[piperazine structures and related cyclic amine structures with $R_1$, $R_2$, X]

$R_1$ and $R_2$ are, independently, hydrogen or lower alkyl;
$R_3$ is $(CH_2)q-N{\overset{R_1}{\underset{R_2}{}}}$;

X is $CH_2$, $NR_1$, O, S;
n is 1 to 4;
q is 2 to 4;
$R_4$ and $R_5$ are independently selected from the group of hydrogen, lower alkyl, halogen, amino, hydroxy, cyano, trifluormethyl, or lower alkoxy;
$R_6$ is a moiety of the formula:

$$-\overset{O}{\underset{\|}{C}}-Ar$$

Ar is a moiety selected from

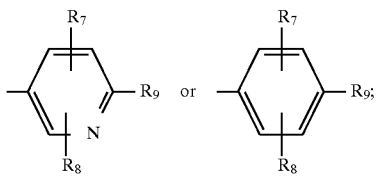

R$_7$ and R$_8$ are independently selected from hydrogen or halogen; lower alkoxy;

R$_9$ is a moiety of the formula:

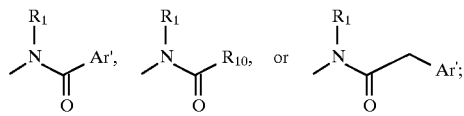

R$_{10}$ is a moiety of the formula

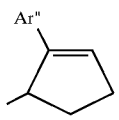

Ar' is a moiety selected from

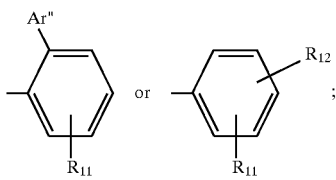

R$_{11}$ and R$_{12}$ are selected independently from hydrogen, F, Cl, Br, cyano, lower alkyl, lower alkoxy, phenoxy, or trifluoromethyl;

Ar" is selected from phenyl 2-pyridyl or a five membered aromatic heterocyclic ring having one or two heteroatoms selected from N, O, S;

or a pharmaceutically acceptable salt thereof.

3. A compound of claim 1 having the formula:

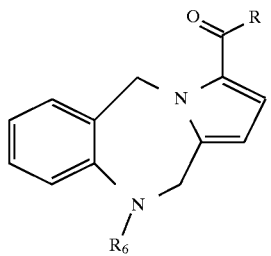

wherein

R is selected from OH, NR$_1$R$_3$ or

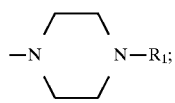

R$_1$ and R$_2$ are independently hydrogen or lower alkyl;

R$_3$ is

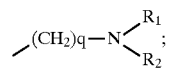

q is 2 to 4;
R$_6$ is a moiety of the formula:

Ar is a moiety selected from

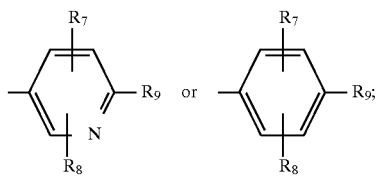

R$_7$ and R$_8$ are independently selected from hydrogen or halogen;

R$_9$ is

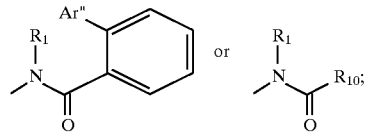

R$_{10}$ is a moiety of the formula;

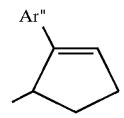

Ar" is selected from phenyl or a five membered aromatic heterocyclic ring having one or two heteroatoms selected from N, O, S;
or a pharmaceutically acceptable salt thereof.

4. A compound of claim 1 which is 10-[2-Chloro-4-(5-fluoro-2-methyl-benzoylamino)-benzoyl]-10,11-dihydro-5H-pyrrolo[2,1-c][1,4]benzodiazepine-3-carboxylic acid or a pharmaceutically acceptable salt thereof.

5. A compound of claim 1 which is 10-[2-Chloro-4-(5-fluoro-2-methyl-benzoylamino)-benzoyl]-10,11-dihydro-5H-pyrrolo[2,1-c][1,4]benzodiazepine-3-carboxylic acid, potassium salt (1:1).

6. A compound of claim 1 which is N-{3-Chloro-4-[3-(N',N'-dimethyl-hydrazinocarbonyl)-5H,11H-pyrrolo[2,1-c][1,4]benzodiazepine-10-carbonyl]-phenyl}-5-fluoro-2-methyl-benzamide or a pharmaceutically acceptable salt thereof.

7. A compound of claim 1 which is 2-[[10-[2-Chloro-4-[(5-fluoro-2-methylbenzoyl)amino]bnezol]-10,11-dihdro-5H-pyrrolo2,1-c][1,4]benzodiazepin-3-yl]carbonyl]-1,1,1-trimethylhydrazinium iodide or a pharmaceutically acceptable salt thereof.

8. A compound of claim 1 which is 2-[[10-[2-Chloro-4-[(5-fluoro-2-methylbenzoyl)amino]benzoyl]-10,11-dihydro-5H-pyrrolo[2,1-c][1,4]benzodiazepin-3-yl]hydroxymethylene]-1,1,1-trimethylhydrazinium inner salt or a pharmaceutically acceptable salt thereof.

9. A compound of claim 1 which is N-[5-[3-trichloromethylcarbnyl]-[5H-pyrrolo-[2,1-c]-[1,4]-benzdiazapin-10(11H)-yl]carbonyl]-2-chlorophenyl]-2-phenyl-benzamide or a pharmaceutically acceptable salt thereof.

10. A compound of claim 1 which is 10-{4-[(Bipheny-2-carbonyl)-amino]-2-chloro-benzoyl)-10,11-dihydro-5H-benzo[e]pyrrolo[1,2-a][1,4]diazepine-3-carboxylic acid or a pharmaceutically acceptable salt thereof.

11. A compound of claim 1 which is 10-(4-[(Biphenyl-2-carbonyl)-amino]-2-chloro-benzoyl)-10,11-dihydro-5H-benzo[e]pyrrolo[1,2-a[1,4]diazepine-3-carboxylic acid-piperazine-N-methyl amide or a pharmaceutically acceptable salt thereof.

12. A compound of claim 1 which is 10-{4-[(Biphenyl-2-carbonyl)-amino]-2-chloro-benzoyl}-10,11-dihydro-5H-pyrrolo[2,1-c][1,4]benzodiazepine-3-carboxylic acid (2-dimethylamino-ethyl)-methyl-amide or a pharmaceutically acceptable salt thereof.

13. A compound of claim 1 which is Biphenyl-2-carboxylic acid{3-chloro-4-[3-(4-piperidinyl-piperidine-1-carbonyl)-5H,11H-pyrrolo[2,1-c][1,4]-benzodiazepine-10-carbonyl]-phenyl}-amide or a pharmaceutically acceptable salt thereof.

14. A compound of claim 1 which is Biphenyl-2-carboxylic acid{3-chloro-4-[3-(4-dimethylamino-piperidine-1-carbonyl)-5H,11H-pyrrolo[2,1-c][1,4]benzodiazepine-10-carbonyl]-phenyl}-amide or a pharmaceutically acceptable salt thereof.

15. A compound of claim 1 which is Biphenyl-2-carboxylic acid{3-chloro-4-[3-(4-methyl-piperazine-1-aminocarbonyl)-5H,11H-pyrrolo[2,1-c][1,4]benzodiazepine-10-carbonyl]-phenyl}-amide or a pharmaceutically acceptable salt thereof.

16. A compound of claim 1 which is 10-{4-[(Biphenyl-2-carbonyl)-amino]-2-chloro-benzoyl}-10,11-dihydro-5H-pyrrolo[2,1-c][1,4]benzodiazepine-3-carboxylic acid (2-dimethylamino-ethyl)-amide or a pharmaceutically acceptable salt thereof.

17. A compound of claim 1 which is Biphenyl-2-carboxylic acid{3-chloro-4-[3-(4-morpholino-piperidine-1-carbonyl)-5H,11H-pyrrolo[2,1-c][1,4]benzo-diazepine-10-carbonyl]-phenyl}-amide or a pharmaceutically acceptable salt thereof.

18. A compound of claim 1 which is 10-(4-[(Biphenyl-2-carbonyl)-amino]-2-methoxy-benzoyl)-10,11-dihydro-5H-benzo[e]pyrrolo[1,2-a[1,4]diazepine-3-carboxylic acid piperazine-N-methyl amide or a pharmaceutically acceptable salt thereof.

19. A compound of claim 1 which is 10-(4-[(Biphenyl-2-carbonyl)-amino]-2-methoxy-benzoyl)-10,11-dihydro-5H-benzo[e]pyrrolo[1,2-a[1,4]diazepine-3-carboxylic acid-1,1-dimethyl hydrazide or a pharmaceutically acceptable salt thereof.

20. A compound of claim 1 which is 10-{4-[(Biphenyl-2-carbonyl)-amino]-2-chloro-benzoyl)-10,11-dihydro-5H-pyrrolo[2,1-c][1,4]benzodiazepine-3-carboxylic acid (glycyl)-amide or a pharmaceutically acceptable salt thereof.

21. A compound of claim 1 which is 10-[2-Chloro-4-(2-thiophen-2-yl-benzoylamino)-benzoyl]-10,11-dihydro-5H-pyrrolo[2,1-c][1,4]benzodiazepine-3-carboxylic acid-1,1-dimethyl hydrazide or a pharmaceutically acceptable salt thereof.

22. A compound of claim 1 which is 10-[2-Chloro-4-(3-pyridin-2-yl-benzoylamino)-benzoyl]-10,11-dihydro-5H-pyrrolo[2,1-c][1,4]benzodiazepine-3-carboxylic acid-piperazine-N-methyl amide or a pharmaceutically acceptable salt thereof.

23. A compound of claim 1 which is 10-[2-Chloro-4-(4-pyridin-2-yl-benzoylamino)-benzoyl]-10,11-dihydro-5H-pyrrolo[2,1-c][1,4]benzodiazepine-3-carboxylic acid(2-dimethylamino-ethyl)-methyl-amide or a pharmaceutically acceptable salt thereof.

24. A compound of claim 1 which is 10-[2-Chloro-4-(2-pyridin-2-yl-benzoylamino)-benzoyl]-10,11-dihydro-5H-pyrrolo[2,1-c][1,4]benzodiazepine-3-carboxylic acid-piperazine-N-methyl amide or a pharmaceutically acceptable salt thereof.

25. A compound of claim 1 which is 10-[2-Bromo-4-(2-pyridin-2-yl-benzoylamino)-benzoyl]-10,11-dihydro-5H-pyrrolo[2,1-c][1,4]benzodiazepine-3-carboxylic acid-1,1-dimethyl hydrazide or a pharmaceutically acceptable salt thereof.

26. A compound of claim 1 which is 10-[2-Chloro-4-(8-quinoloinylylamino)-benzoyl]-10,11-dihydro-5H-pyrrolo[2,1-c][1,4]benzodiazepine-3-carboxylic acid-piperazine-N-methyl amide or a pharmaceutically acceptable salt thereof.

27. A compound of claim 1 which is 2-Phenyl-cyclopent-1-enecarboxylic acid[3-chloro-4-(3-carboxylic acid(2-dimethylamino-ethyl)-methyl-amide-5H,11H-pyrrolo[2,1 c][1,4]benzodiazepine-10-carbonyl)-phenyl]-amide or a pharmaceutically acceptable salt thereof.

28. A compound of claim 1 which is 10-(4-[(Biphenyl-2-carbonyl)-amino]-2-chloro-benzoyl}-10,11-dihydro-5H-pyrrolo[2,1-c][1,4]benzodiazepine-3-carboxylic acid (glycyl)-amide or a pharmaceutically acceptable salt thereof.

29. A pharmaceutical composition useful for treating disease in a mammal characterized by excess renal reabsorption of water, the pharmaceutical composition comprising an effective amount of a compound of claim 1, or a pharmaceutically acceptable salt, ester or prodrug form thereof, and a suitable pharmaceutical carrier.

30. The pharmaceutical composition of claim 29 wherein the disease in a mammal characterized by excess renal reabsorption of water is congestive heart failure, nephrotic syndrome, hyponatremia, coronary vasospasm, cardiac ischemia, renal vasospasm, liver cirrhosis, the Syndrome of Inappropriate Anti-Diuretic Hormone Secretion, brain edema, cerebral ischemia, or cerebral hemorrhage-stroke.

31. A method for treating disease in a mammal characterized by excess renal reabsorption of water, the method comprising administering to a mammal in need thereof an effective amount of a compound of claim 1, or a pharmaceutically acceptable salt, ester or prodrug form thereof, and a suitable pharmaceutical carrier.

32. The method of claim 31 wherein the disease in a mammal characterized by excess renal reabsorption of water is congestive heart failure, nephrotic syndrome, hyponatremia, coronary vasospasm, cardiac ischemia, renal vasospasm, liver cirrhosis, the Syndrome of Inappropriate Anti-Diuretic Hormone Secretion, brain edema, cerebral ischemia, or cerebral hemorrhage-stroke.

* * * * *